United States Patent [19]

Galen et al.

[11] Patent Number: 5,515,176
[45] Date of Patent: May 7, 1996

[54] INTERACTIVE FAX IMAGING

[75] Inventors: Peter M. Galen; David L. Burton; William E. Saltzstein; Lawrence Hileman, all of McMinnville, Oreg.

[73] Assignee: Hewlett-Packard Company, Palo Alto, Calif.

[21] Appl. No.: 352,300

[22] Filed: Dec. 8, 1994

Related U.S. Application Data

[63] Continuation of Ser. No. 949,415, Sep. 21, 1992.

[51] Int. Cl.$^6$ .............................. H04N 1/00; H04N 1/387
[52] U.S. Cl. ..................... 358/403; 358/450; 358/452; 128/904; 395/100; 395/114; 395/148
[58] Field of Search ..................... 358/400, 403, 358/406, 442, 444, 450, 452, 453, 443, 448; 128/696, 904; 395/100, 114, 117, 118, 135, 140, 147, 148, 149; 364/413.01, 413.02, 413.05, 413.06; 345/201

[56] References Cited

U.S. PATENT DOCUMENTS

| | | | |
|---|---|---|---|
| 4,802,008 | 1/1989 | Walling | 358/406 |
| 4,827,330 | 5/1989 | Walsh et al. | 358/452 |
| 4,833,625 | 5/1989 | Fisher et al. | 345/201 |
| 5,111,306 | 5/1992 | Kanno et al. | 358/403 |
| 5,222,157 | 6/1993 | Yoneda et al. | 358/403 |
| 5,226,431 | 7/1993 | Bible et al. | 128/696 |

Primary Examiner—Scott A. Rogers
Assistant Examiner—Thomas D. Lee

[57] ABSTRACT

A remote interactive fax imaging system is disclosed. Stored data, including graphic data, is converted to fax format and transmitted to a remote site. The transmitted image includes machine-readable identification data for identifying the underlying database, and a blank dedicated comment field. At the remote site, a user reviews the faxed image and enters annotations within the dedicated field. The annotated image is faxed back to the originating site. At the originating site, the identifying data is read to associate the annotated image with the original underlying database. The dedicated field area of the return image is added into the data base, thereby forming a complete, annotated record without degrading the original data. The disclosed apparatus and methodology are especially useful, for example, for timely over-reading of electrocardiograph data by a physician at a location remote from the patient.

20 Claims, 6 Drawing Sheets

INTERACTIVE FAX IMAGING

This is a continuation, of application Ser. No. 07/949,415, filed 21 Sept. 1992.

A portion of the disclosure of this patent document contains material which is the subject of copyright protection. The copyright owner has no objection to facsimile reproduction by anyone of the patent document or the patent disclosure, as it appears in the U.S. Patent and Trademark Office file or records, but otherwise reserves all copyrights whatsoever.

FIELD OF THE INVENTION

This invention relates to digital communication of image data, preferably by facsimile ("fax") and, more specifically, relates to a remote interactive medical imaging system and method to allow review of medical image data, such as an electrocardiograph, at a site remote from the patient. Comments and annotations made by a reviewing physician at the remote site, such as diagnoses, treatment recommendations and medication prescriptions, are transmitted from the remote site by return fax, and the annotations are added back into the original electrocardiograph database without compromising the original image data.

Fax transmission of image data is now commonplace. One application of fax is transmission of medical waveform data for accessing off-site diagnostic expertise in a timely manner. For instance, emergency rooms or private physicians may require quick, expert electrocardiograph (ECG) diagnoses.

In the prior art, ECGs have been faxed to remote sites using conventional fax machines, which optically scan a hard copy print of the subject ECG. The optical scanning process results in reduced ECG quality at the receiving end, making accurate physician review difficult.

Better quality transmissions can be obtained by transmitting digital data representing the ECG image directly from the cardiograph (or from a digital storage device such as a floppy disk), thereby eliminating the intermediate optical scanning step. This direct transmission produces a faxed ECG copy of nearly original quality, i.e. of the same quality as a hard copy ECG printed locally. Direct digital ECG may be accomplished by configuring a digital cardiograph with suitable hardware and software, described in greater detail below, and coupling the system to a fax modem, or any CCITT Group 3 fax machine or the like. A commercial electrocardiograph system having direct digital fax capability is the Hewlett-Packard Model M1700A PageWriter XLi Cardiograph, equipped with the optional HP Model M1756A Direct Digital ECG Fax.

Once the facsimile medical data, for example an ECG copy, is received at a remote location, it would be desirable to obtain an appropriate record of the physician's review or "over reading" of that ECG copy. Good practices from both medical and legal viewpoints suggest that the reviewing physician's diagnosis be made in writing. It is particularly important, and often a legal requirement, that the physician's prescription for medications be in writing and signed by the physician. Moreover, it is critically important the physician's diagnosis or other comments, prescription of medications, signature and the like be accurately associated with the original ECG copy and thereby associated with the right patient.

A reviewing physician (at a remote site) may make notes and comments on an ECG hard copy itself, and then fax the annotated copy back to the originating site. This approach has several drawbacks. First, the ECG itself, having been faxed to the remote site and then return faxed, is degraded to where it is difficult, if not impossible, to interpret. Second, while the return annotated fax may be associated manually with the original record, this introduces a risk of error. Third, modifications or amendments to the original ECG database to reflect the reviewing physician's comments likewise must be entered manually. This leads to a further risk of error arising from visual interpretation of a facsimile of the reviewing physician's handwritten notes.

In view of the foregoing background, the need remains for communicating image data, such as an ECG, to a remote site for review, and receiving an annotated copy of the ECG by return fax, without degrading the image quality.

A need also remains for reliably associating such a return fax with the original record, to avoid treating a patient according to instructions intended for another patient, the results of which could be disastrous.

A need further remains for an accurate way to incorporate the offsite reviewing physician's diagnosis, treatment notes, prescriptions and the like into the original ECG database, so that the record is then complete, permanent and accurate.

SUMMARY OF THE INVENTION

The present invention includes a method of interactive imaging between an instrument site and a remote site. The process includes first recording an ECG of a patient at the instrument site. The recorded ECG data is stored in a digital database, the database also including unique identification data for identifying the database. This may include patient demographic data, and the date of time of recording, for example. The next step is converting the ECG data so as to form a fax image. Alphanumeric data, such as the identification data, is converted to bit map image form for inclusion in the fax image. The completed image is faxed to the remote site for review, such as over reading by a physician.

At the remote site, the image is annotated for example by inserting a comment indicating diagnosis or recommended treatment. Then the annotated ECG image is faxed back to the instrument site. At the instrument site, the method next calls for recovering the identification data from the annotated image to identify the database; and updating the identified database by moving a portion of the annotated image containing the comment into the identified database.

Another aspect of the invention calls for encoding the identification data into a machine-readable form, such as bar-code form. This has the advantage of facilitating recovery of the identification data after faxing from and back to the instrument site.

A further aspect of the invention calls for providing a blank dedicated area at a predetermined location within the fax format image for comments. Thus, annotating the fax image includes inserting a comment within the dedicated area. After the annotated image is received back at the instrument site, the system copies from the annotated image a region corresponding to the dedicated area and adds it to the database, thereby extracting the comment from the annotated image. In this way, the reviewing physician's comments are added to the database without overwriting or othewise corrupting the original data.

The foregoing and other objects, features and advantages of the invention will become more readily apparent from the following detailed description of a preferred embodiment which proceeds with reference to the drawings.

Appendix A is an example of a computer program for rasterizing digital data.

Appendix B is a listing of a computer program for fax encoding rasterized digital data.

Appendix C is a listing of a computer program for converting the resolution of digital data to fax to a standard CCITT Group 3 fax resolution or format.

DETAILED DESCRIPTION OF THE PREFERRED EMBODIMENT

1. Overview and Hardware Description

Figure 1:
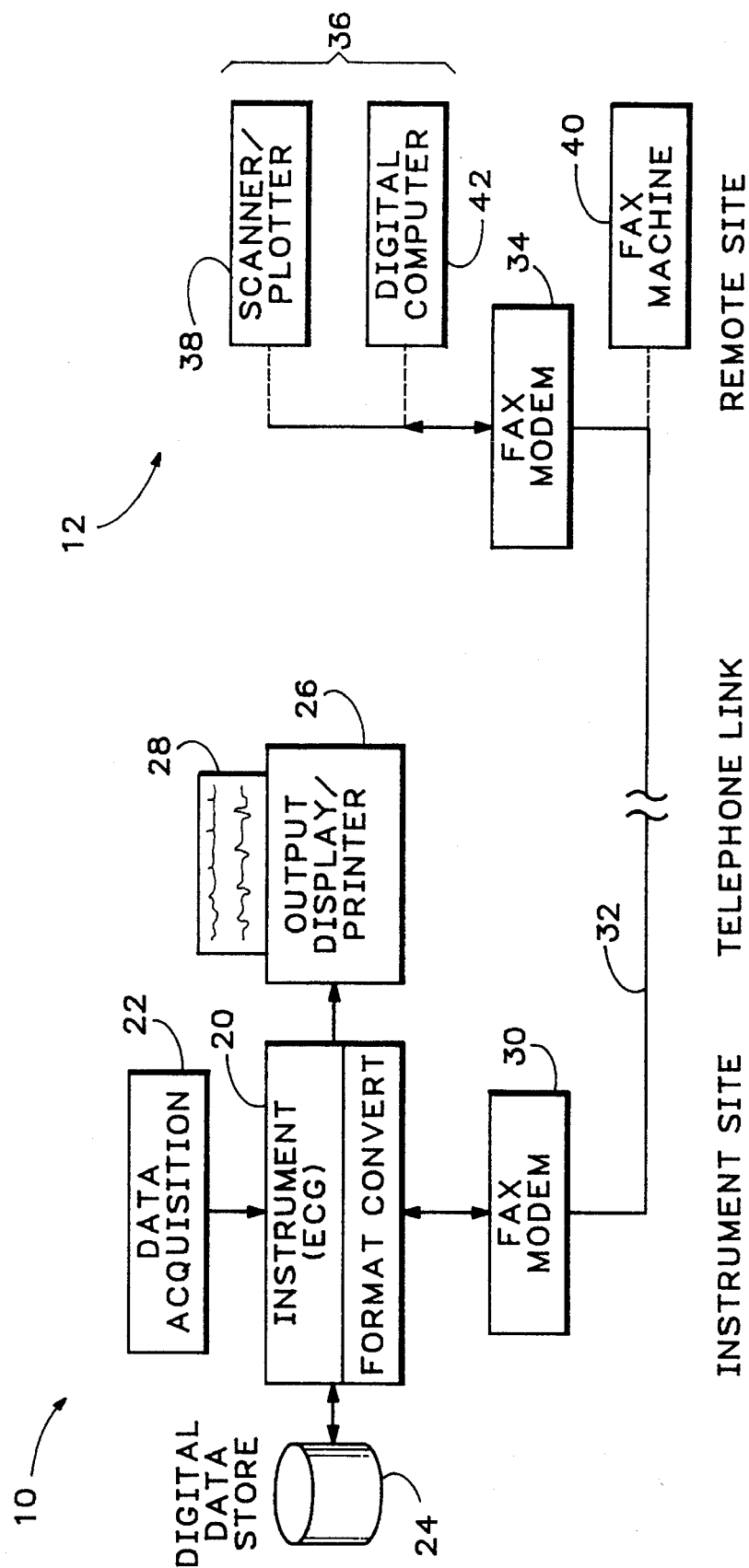
FIG. 1 is a block diagram of an interactive fax imaging system according to the invention.

FIG. 1 is a block diagram of an interactive fax imaging system according to the present invention. The figure depicts a first set of equipment 10 located at an instrument site and a second set of equipment 12 to be located at a remote site. "Instrument site" means a site where data is acquired and/or stored. In the latter case, no original data acquisition apparatus need be present. In the embodiment illustrated, data acquisition apparatus is provided. Thus, an instrument 20 is located at the instrument site for acquiring data. Acquired data may be analog and/or digital, but in any event includes data which is usefully represented in graphic form for visual inspection, such as a voltage waveform. For example, instrument 20 may be an electrocardiograph (ECG) or electronic test equipment such as an oscilloscope. Suitable data acquisition apparatus 22 is coupled to instrument 20 to provide input data. In the case of an ECG instrument, the data acquisition apparatus 22 may include patient leads. In the case of electronic instrumentation, data acquisition apparatus 22 may include suitable input probes, A-to-D converters or a port coupled to a bus, such as an IEEE 488 interface bus, for interconnecting test equipment.

Instrument 20 is coupled to suitable output device 26 such as a video display terminal and/or a printer. Reference number 28 indicates a hard copy report produced by the printer. A digital data storage device such as a hard disk drive 24 is coupled to instrument 20 for storing acquired data. Floppy or optical disk, magnetic tape or other storage media may be used as well. Acquired data from a particular test or procedure, for example an ECG, is stored in a corresponding database.

Instrument 20 includes means (labeled "Format Convert") for converting stored data from a predetermined digital data storage format, called the internal format, into a standard fax format such as the CCITT Group 3 fax format. Format conversion preferably is carded out in software. The Appendices provide an example of computer programs to provide this function. This step may be omitted where digital communication other than fax is used. A fax modem 30 or the like is connected to instrument 20 for transmitting and receiving images in the fax format. The fax modem 30 is coupled over a telephone link 32 to provide communication with a selected remote site. Any number of remote sites may used. One (or more) remote sites is accessed by controlling the fax modem to dial the corresponding telephone number(s), as is known.

Apparatus 12 are located at a remote site and include a second fax modem 34 connected to the telephone link for fax communication with the instrument site. Although a conventional telephone link is suggested by the drawing, wireless telephone communication such as cellular technologies may be used. In fact, any means for image data communication is applicable. Fax communication is the presently preferred embodiment because of the widespread availability of fax equipment.

The remote site fax modem 34 is connected to suitable apparatus 36 for converting a received fax image to visual form for display to a user, and for faxing an image back to the instrument site. Or, a conventional fax machine 40 may be provided (which typically includes an internal fax modem). Fax modem 34 may be coupled to a scanner and plotter 38. The plotter could be used to provide a hard copy printout corresponding to a received fax image, and conversely, the scanner used to input a hard copy image for faxing to the instrument site.

Another alternative is a digital computer 42 coupled to fax modem 34 and having suitable software to allow both display and editing of graphical images, and faxing of such images via the fax modem 34. The fax modem may be internal to the digital computer. Other variations are possible, the essential functions being that the remote site is equipped (a) to receive a fax image (or "report") and display the corresponding report to a user; (b) modify or annotate the received report (which may be done manually), as explained further below and; (c) transmit the annotated report in fax format back to the instrument site.

2. Data Types and ECG Reports

At the instrument site, acquired data is stored in digital form in a database in instrument 20 (or data store 24). Various internal formats may be used for this purpose, depending on the particular application and the available hardware. To illustrate, acquired data may include one or more analog waveforms representing voltage measurements. Digital data representing each waveform may be formatted as a series of bytes in the database, each byte having a value corresponding to an instantaneous amplitude of the waveform, there being some predetermined time period per byte, or sample rate, so that the waveform can be reconstructed from the stored digital data. The particulars of analog-to-digital and digital-to-analog conversion are known, as well as various means for storing and compressing digital data, so these need not be discussed further. Another type of data is text, which may be stored by conventional means, such as ASCII encoding.

In the ECG example (below), text fields may include patient name, age, sex, blood pressure, etc. which we call demographics. A third type of data may be a grid for superimposing on waveform data. All three of these types of data are used in the preferred embodiment, as further described below, though the invention and its utility are not limited to any particular types of data or database formats.

Figure 2:
FIG. 2 is an illustration of a graphical image, here an ECG report, which is a product of the system of FIG. 1.

FIG. 2 is an illustration of an electrocardiograph (ECG) report produced by the instrument site apparatus 10 of FIG. 1. The term "report" as used herein means a visual representation of the contents of an underlying database. A report may appear in a screen display or a "hard copy". The illustrated ECG report 50 contains several items or fields of information. For example, it includes identification fields 52 that identify the patient by name, date of birth, patient number, etc. Additional identification fields specify the particular ECG procedure by the date and time at which it was recorded. Each such item of information is stored in a corresponding field in the underlying database. For alphanumeric identification information, the data may conveniently be stored in ASCII format.

Selected identification data is encoded into a form that is reliably machine-readable, such as a bar code field 54. The bar code field 54 must contain sufficient information to uniquely identify the particular database underlying this ECG record. This is because the database will later be automatically updated based on information received by fax from a remote site. Since a bar code is graphical, it may be stored in the database, for example, in a bit-mapped format field. Alternatively, to save storage space, the bar code may be generated at fax transmission (or print) time. The bar code need not be stored in the database since it is redundant of other fields. Other machine-readable coding schemes may be used. The coding must provide for accurate identification of the ECG record even after it is faxed to the remote site and return faxed to the instrument site.

The ECG 50 may also include additional fields 56 identifying the instrument by location and identifying the operator. Various other items of information shown on the ECG, such as the patient's heart rate, rhythm information and other ECG data will be useful to the reviewing physician at the remote site. Each of these items is stored in a corresponding field in the database as well. All of the alphanumeric or text portions of the report, taken together, are referred to hereinafter as the "text report".

ECG 50 further includes one or more voltage waveforms, for example waveforms 62, 64, 66 as is conventional for electrocardiographic data. A rectangular grid 60 is superimposed with the waveforms. Additional alphanumeric fields may be stored in the database and displayed in the ECG report, such as cardiograph settings for speed and lead sensitivity, etc. as indicated generally below grid 60 at reference numeral 68.

3. Comment Fields

A dedicated field 70 is provided for a user at the remote site, for example a reviewing physician, to write comments based on her review of the ECG. Dedicated field 70 is a predefined area on the ECG report reserved for this purpose. It is left blank in the original ECG transmitted to the remote site. The reviewing physician's comments may include, for example, diagnosis, recommended treatment and/or prescribed medication. The size and shape of the dedicated field are not critical. A larger field allows for more comprehensive comments by the reviewing physician, but this advantage must be traded off against the corresponding loss in area available for display of waveforms and other patient data.

The comment field need not be fixed in size or positioned on the report in advance. It may be defined by the reviewer at the remote site. For example, a comment field may be defined by one or more delimit characters. For this purpose, the delimit character(s) must be predefined. For example, a predefined delimit character may be use to indicate one corner of a comment field. The dimensions of the field may be predefined, and the field will be assumed to be a rectangle extending from the corner indicated by the delimiter.

Alternatively, a first delimit mark may be used to indicated the beginning of the comment area, and a second delimit mark used to indicate the end of the comment area. To illustrate, referring to FIG. 2, the comment field 70 is defined by a first delimit mark to the left of the field (asterisk followed by exclamation point) 74, and a second delimit mark 76 to the right of the field, as shown (exclamation point followed by asterisk). In that case, the system assumes a predefined width of the comment field, for example one-half to one inch. Other methods of defining an area using one or more delimiters may be used. The selected delimiter(s) should be easily recognized by software, even if handwritten. Or, the delimiter may be applied using a preprinted adhesive label or a rubber stamp. In practice, a report probably would not include a dedicated field 70 and delimiters 74,76 defining the same field, as shown in the drawing. Both are shown in the same report here for illustration. However, a reviewer could add a delimited field if necessary, for example where the dedicated field is too small.

The reviewing physician's comments may be handwritten on a hard copy or otherwise inserted within the dedicated field 70. Where the selected remote site equipment 12 includes a computer 42 for reviewing and editing the fax image on screen (see FIG. 1), the reviewing physician may type remarks on the computer keyboard so as to insert them within the dedicated field 70. Application software for editing a graphic image on a computer is known. Under some circumstances, however, it is preferable that the physician's remarks be handwritten and signed by the physician. This may be essential for creating a legal record of the physician's diagnosis and recommended treatment.

In the event that the reviewing physician defines a comment field that overlaps other data, several options may be implemented. For example: (1) ignore the comments outside a predefined maximum area; (2) overwrite other data to so as to display all of the physician's comments; (3) overwrite other data except within predefined "protected zones" which must be displayed in their original form. Other variations may be implemented, preferably in software. The system may be configurable so as to allow the user or operator to select among these or other options. Another extension is to provide permission protection of the underlying database. For example, the entire record may be "read only" except for a dedicated field. Or, selected remote sites (or physicians) could have write permission to alter other parts of the record. A physician then could elect to overwrite a non-essential part of the record with comments.

4. Fax Transmission Process

Figure 3:
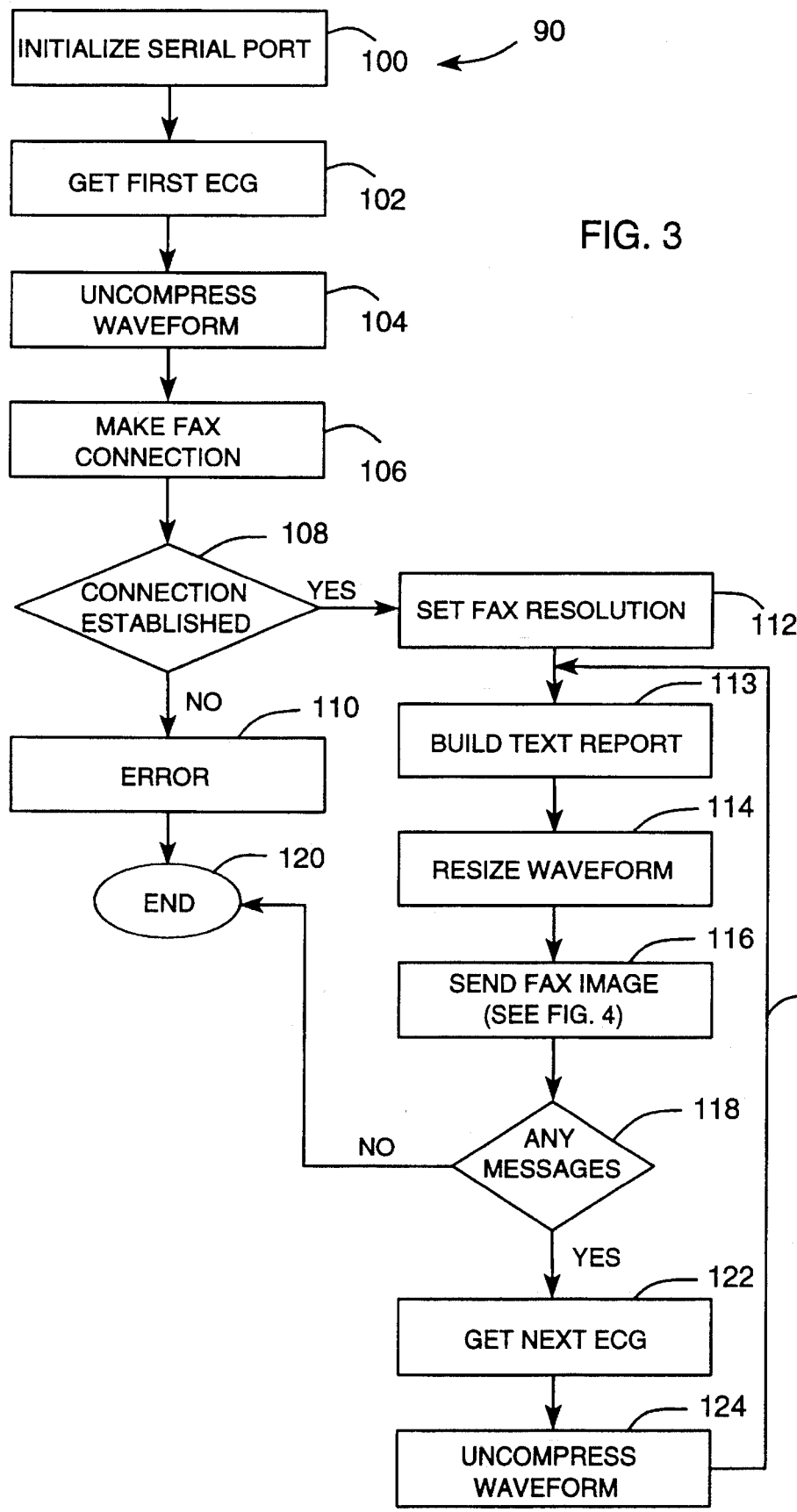
FIG. 3 is a flowchart of a fax transmission process for sending an ECG report.

FIG. 3 is a flow diagram illustrating a fax transmission process according to the invention, for producing a report of the type illustrated by FIG. 2. The method of FIG. 3 preferably is implemented in software which is arranged to control a microprocessor and associated circuitry or other apparatus such as a digital computer for executing a series of instructions. The first step 100 is to initialize a serial port, which is a hardware connection for coupling the instrument to the fax modem. The next step 102 is to read a first ECG or other digitally stored database. The database may be stored in RAM, on a hard disk, floppy disk or other digital storage medium. The digital data is uncompressed 104 if necessary. The particulars of this step will depend upon what compression algorithm, if any, is employed.

Next the fax modem is activated, step 106, to establish a fax connection with a desired remote site via an appropriate telephone link. A test 108 determines whether or not a fax connection has been established. If not, an error routine 110 may make another attempt to establish a fax connection, try an alternate telephone number or notify the user of the problem. If no connection is established, the process ends 120.

If and when a fax connection is established, the fax resolution is set in step 112. The fax resolution is selected by a dialogue between the fax equipment at the two sites according to predetermined protocols such as the CCITT Group 3 standard. After the fax resolution has been determined, the next step is to build a text report 113. This step converts textual (alphanumeric) data, such as patient identification, etc., into suitable bit map image form, at the set resolution, using character generator techniques. The text report is formed so as to include a blank comment field reserved for comments (the dedicated field). The text report also includes identifying data in machine-readable form, such as a bar code strip, as noted above.

The next step 114 is to resize the waveform(s) so as to fully utilize the available fax resolution (determined in step 112 above). This step refers to the waveforms such as 62, 64 in FIG. 2. Next the fax image is transmitted 116 to the remote site. Details of sending the fax image are described below with regard to FIG. 4. Following transmission, a test 118 is executed to determine whether there are any messages from the fax modem. Such messages may indicate, for example, that part of the transmission was unsuccessful and should be resent. If there are no messages, the process is completed and ends at 120.

Step 122 is to load the next ECG from memory for processing. The ECG waveform is uncompressed 124 and then the steps of building a text report 112, resizing the waveform 114, and transmitting the fax image 116 are repeated, as indicated by the loop path 126 shown in the flowchart. Additional pages or ECGs thus may follow in the same transmission, without repeating the initial handshaking delay incurred in steps 108, 112.

5. Forming Fax Format Data

Figure 4:
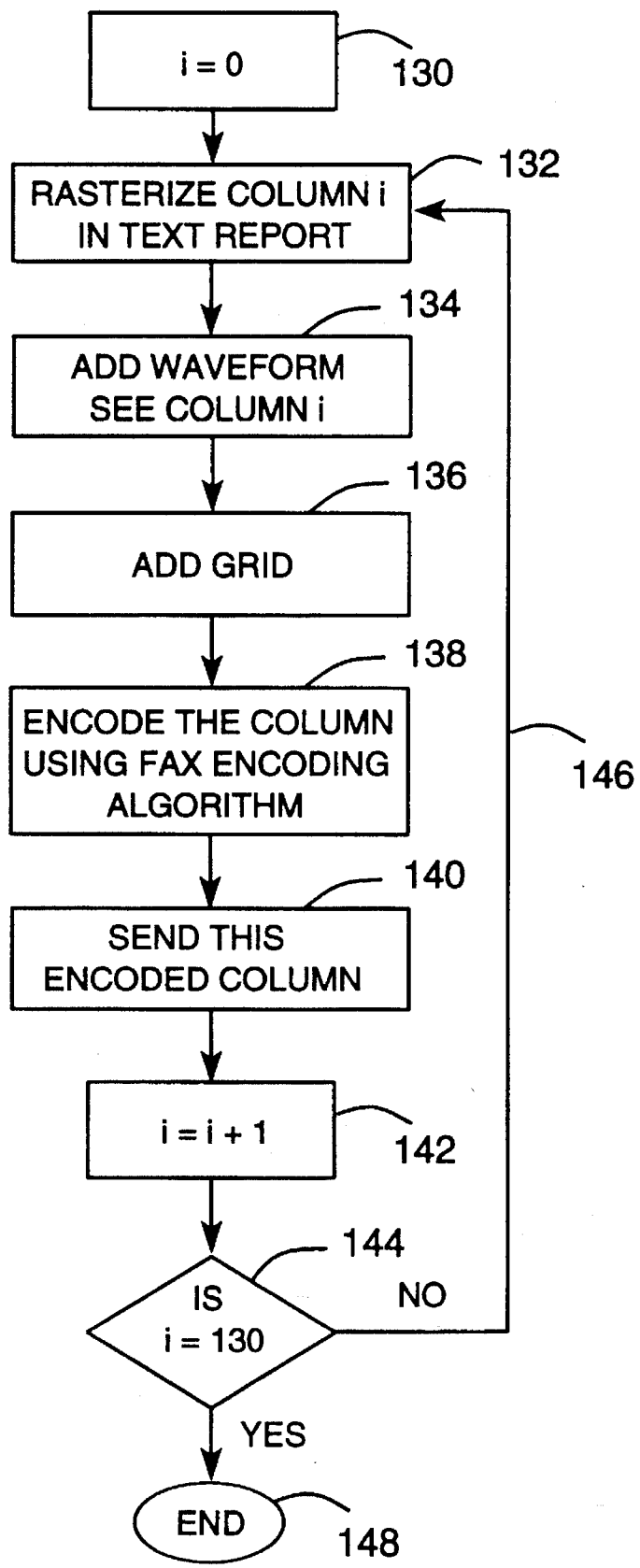
FIG. 4 is a flowchart showing detail of the "send fax image" step 116 of the flowchart of FIG. 4.

FIG. 4 shows detail of the sending fax image (step 116) of the flowchart of FIG. 3. In general, this process involves three planes of bit map image date—(1) text report; (2) waveforms; and (3) grid. All three planes of data are superimposed, one column at a time, to form data for fax transmission.

It is convenient to begin by defining a column counter "i" and initialize it to zero, step 130. The number of columns used or whether the fax page is divided into columns at all depends on the particular implementation and the size of available memory for processing. 130 columns is a convenient arrangement because a commonly used character size for text is 130 columns of text per line. Beginning in the first column, the first step is to write into that column a series of bits, in other words, a bitmap, of the corresponding portion of the text report, step 132. In other words, assuming that the text report comprises character data, rasterization involves converting each character into a dot matrix or bitmap form and writing that information into a suitable memory or buffer. This is done for the entire column which conveniently is 1728 dots or pixels in length, corresponding to the standard fine mode fax column.

The next step 134 is to add the waveform data corresponding to the current column into the buffer. If the waveform data is already stored in bitmap form, this is simply a matter of overlaying the corresponding portion of the waveform bitmap into the buffer. If the waveform data presently is stored in another form, such as a series of sample values, that data must first be transformed into bitmap format.

Next we add a grid, step 136. The entire grid may be stored as in bitmap form. However, since the grid is regular and predetermined, it may be more efficient use of memory space to provide for adding the grid into the buffer via a simple algorithm. Thus the waveform data and the grid are overlaid along with the text report to complete the bitmap image for the current column.

The next step is to encode the current column 138 for fax transmission. This may be done using known fax compression schemes, such as the modified Huffman Code, to reduce transmission time. Some fax encoding schemes operate on a single dot column at a time. In that event, this encoding step would be repeated for each dot of width of the current column. Other fax encoding schemes encode multiple columns at a time.

Then we transmit the fax encoded data, step 140. Ultimately, the current column of data is reduced to a series of single dot wide columns for serial transmission by fax modem, details of which are known.

Next we increment the column counter, 142, and test whether the counter equals the maximum column number, step 144. When that limit is reached, the fax transmission process is complete, and the process ends, 148. If the limit has not been reached, the process loops 146 back to the rasterization step 132, to begin building the next column of image data. Once again the text, waveform and grid data are overlaid to assemble the desired bitmap image.

An example of a computer program routine for rasterizing the digitally stored data to form fax data is shown in Appendix A. An example of a software routine for fax encoding the rasterized data is set forth in Appendix B. An example of software routine for changing resolution, i.e., resizing the waveform to conform to the fax resolution (step 114 in FIG. 3) is shown in Appendix C.

6. Overall Interactive Methodology with Dedicated Comment Field

Figure 5:
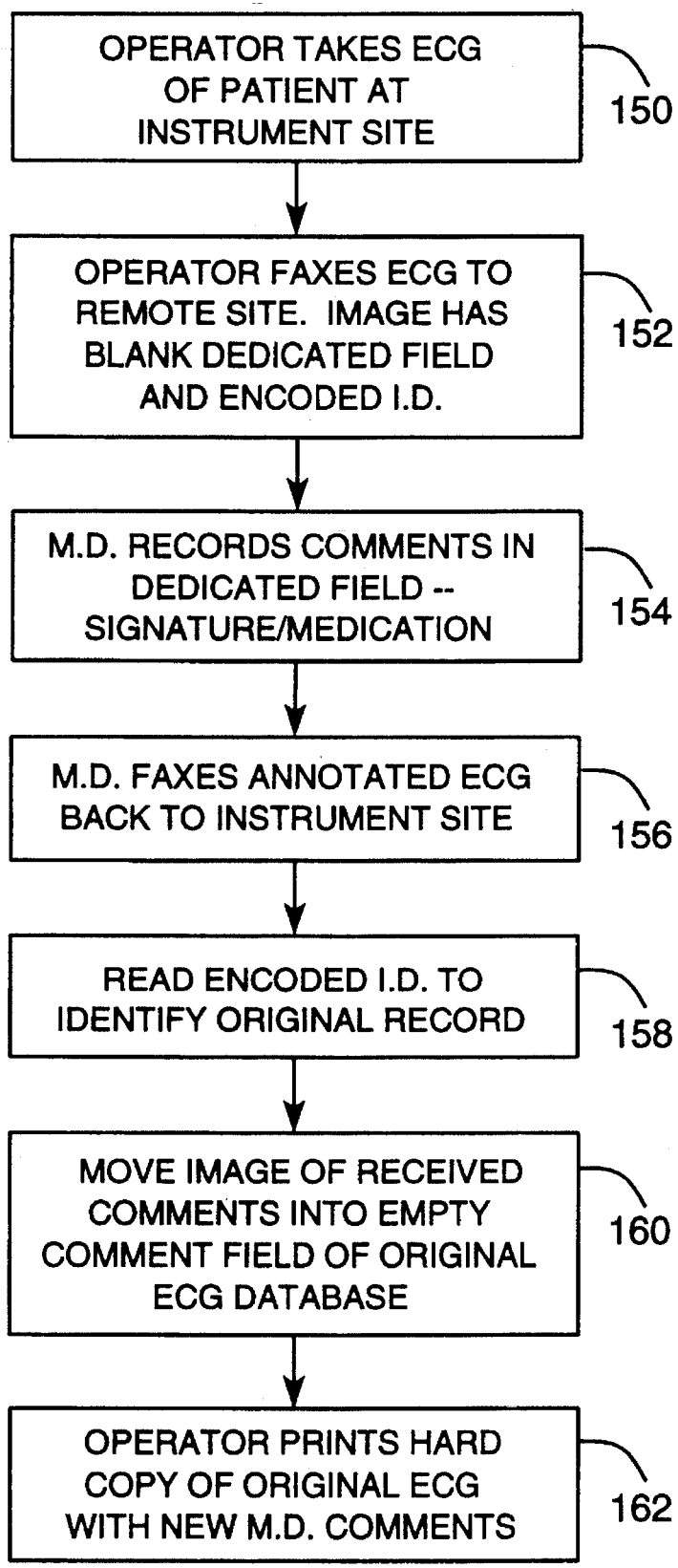
FIG. 5 is a flowchart of an interactive fax imaging method for creating and modifying a database, such as an ECG database, so as to include dedicated field annotations made at a remote site.

FIG. 5 illustrates the overall methodology for using interactive fax imaging according to the invention. The process typically begins by an operator taking an ECG of a patient, step 150. However, the method is equally applicable to image data previously acquired and stored, for example in the data store 24 (FIG. 1). Next, the operator faxes the image, such as an ECG, to a selected remote site, step 152. The faxed image includes a blank comment field and encoded identification data, as discussed above and illustrated in FIG. 2.

A user at the receiving remote site, for example a physician ("M.D."), reviews the ECG, and records comments in the comment field, step 154. As noted, this may be done manually on a hard copy of the ECG, or by computer editing of the fax image. The resulting image we generally call an annotated image or, in the example, an annotated ECG. The annotated ECG is faxed back to the instrument (originating) site, step 156. If hard copy was used at the remote site, the annotated ECG may be scanned by a stand-alone scanner, a conventional fax machine, or the like, for return transmission.

Back at the instrument site, the incoming fax is first decoded to recover the annotated image (a bit map image). The instrument (or computer) next reads the encoded identification data, step 158, to identify the corresponding database from which ECG originated.

The next step is moving the reviewing physician's comments from the received fax into a comment field in the identified database, step 160. In other words, an image of the dedicated field 70 portion of the annotated (return) fax is added into the original database. The remainder of the annotated fax image may be discarded as that image has been degraded by the fax-and-return fax process and, in any event, the original data underlying the remainder of the image already exists in the database. Thus, the updated database now contains all of the original stored data, plus an image of the dedicated comment field recorded at the remote site. Finally, the operator may print out a hard copy of the now annotated ECG record, step 162.

It should be noted that the invention is applicable to single-site use as well. Even where the reviewing physician is local, and perhaps reviewed the ECG even as it was recorded, it is useful to have the physician record annotations and comments on the ECG, as described above, and add that image into the underlying database. This forms a complete, annotated record for subsequent storage, display or transmission for consultation, etc.

The new (annotated) ECG record has the same image quality as it did originally, as the image data has not been altered, except in the dedicated field. The dedicated field image is of acceptable quality because it has been faxed at most only once—from the remote site, where the comments originated, to the instrument site.

Figure 6:
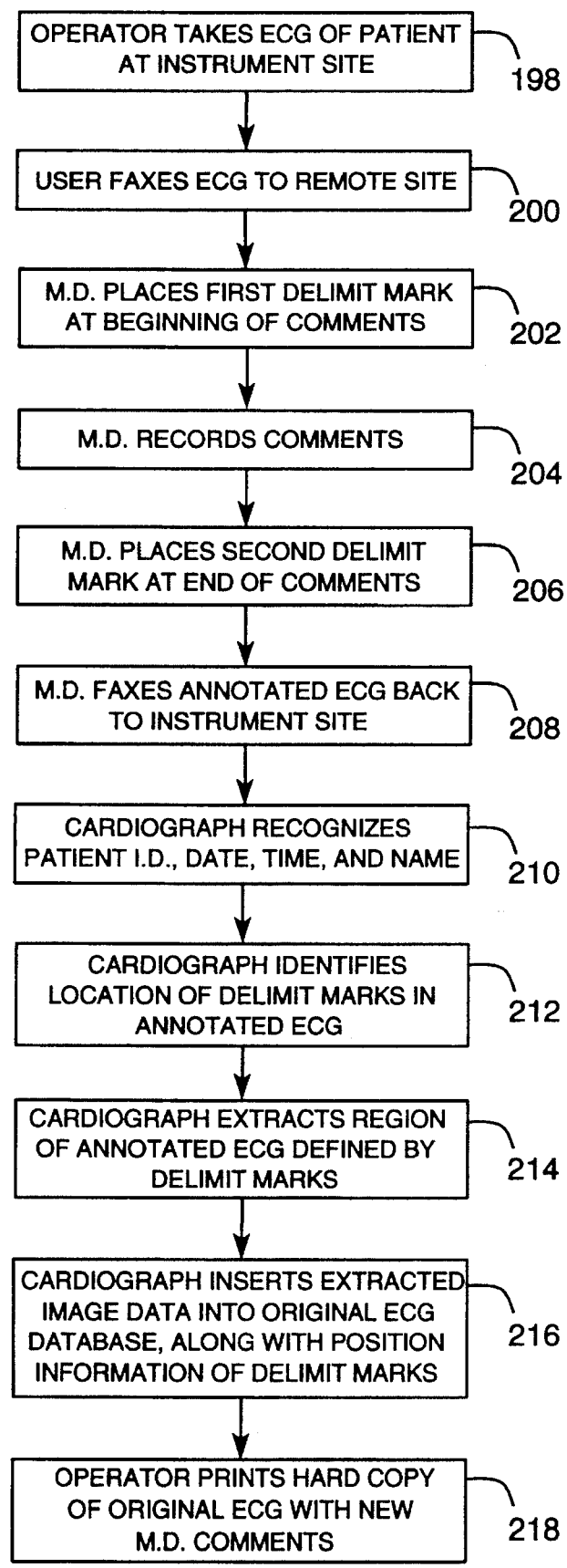
FIG. 6 is flowchart of an interactive fax imaging method for creating and modifying a database, such as an ECG database, so as to include annotations entered within a region defined by delimiter characters on the corresponding ECG report.

FIG. 6 illustrates an interactive fax imaging method in which delimiters are used to identify the location of the comment field.

Referring to FIG. 6, the method begins with acquisition of an ECG or data at the instrument site, step 198. A user faxes the ECG image to a remote site, step 200. In this case, the faxed ECG need not contain a predefined comment area. It should contain machine-readable identifying data, as discussed above.

At the remote site, the reviewing physician places a first delimit mark at the beginning of her comments, step 202, records comments, diagnoses, etc. (step 204), and finally, places a second delimit mark at the end of the comments, step 206. Thus annotated, the ECG is faxed back to the originating site, step 208.

At the originating site, the cardiograph or computer reads the identifying data and recognizes patient identification, date, time, etc. in order to uniquely associate this annotated fax with the corresponding data base (step 210). Next, the cardiograph identifies the location of the first and second delimit marks in the annotated ECG, step 212. Having done so, the system extracts a region of the annotated ECG image defined by the delimit marks. For example, assuming that the delimit marks appear more or less in the same horizontal line, the system may extract a strip of predetermined height along that line between the delimit lines (step 214). The next step is inserting the extracted image data into the original ECG database, along with position information of the delimit marks, step 216. Finally, as before, the operator may print a hard copy of the now annotated ECG, step 218.

Having illustrated and described the principles of our invention in a preferred embodiment thereof, it should be readily apparent to those skilled in the art that the invention can be modified in arrangement and detail without departing from such principles. We claim all modifications coming within the spirit and scope of the accompanying claims.

```
/* ::P:! ey  ry
/*************************************************************

$Logfile:   I:/quarry/fax/vcs/qscfxb10.c_v  $

FILE NAME: QSCFXB10.C          MODULE: FaxBuildSlice

SYSTEM: FAX
    SUBSYSTEM: Build Slice (C) COPYRIGHT HEWLETT-PACKARD COMPANY 1989
              All rights reserved

************** HP CONFIDENTIAL **************

$Date:    29 Jul 1992 20:51:10  $ $Revision:   1.3  $

NOTES:   C Source file
             Created by Lawrence Hileman
---------------------------------------------------------------
    ORIGIN:  Cardiology Business Unit REVISIONS:
    $Log:    I:/quarry/fax/vcs/qscfxb10.c_v  $
**
**    Rev 1.3   29 Jul 1992 20:51:10    Larry_H
** use a pointer, not a defined struct
**
**    Rev 1.2   20 Jun 1992 00:15:06    Larry_H
** function argument change
**
**    Rev 1.1   12 Jun 1992 13:28:28    Larry_H
** add 300 DPI
**
**    Rev 1.0   07 Aug 1991 21:32:00    Larry_H
** Initial revision.

*************************************************************/ include      "QECLH005.H"    /* config defines */
include      "qpcfxint.h"    /* Fax prototypes             */
include      "qecfx010.h"    /* FAX resolutions and report types */ include      "QTCFXV00.H"    /* slice defined */
include      "QVCFXV00.H"    /* extern for slice */

/* check point access */
#include      "QECLSJWL.H"    /* #define check point values */
include      "qvcls02d.h"    /* extern unsigned short check_point */ void FaxBuildSlice( col,res,PageNum,ReportType,Speed,Site )
int col,res,PageNum,ReportType,Speed,Site;
{
        check_point= FAX_FAX_BUILD_SLICE;

if (res == SIZE_FOR_300_RESOLUTION)
              {
              ClearSlice( Slice,COLUMNS_PER_SLICE_300 );
```

```
            CopyOverlap( Slice,COLUMNS_PER_SLICE_300 );
            }
        else
            {
            ClearSlice( Slice,COLUMNS_PER_SLICE );
            CopyOverlap( Slice,COLUMNS_PER_SLICE );
            }

PutTextIntoSlice( col, res, Slice );

if (ReportType == CONFIG_PRT_EXT_MM)
                return;

if ((PageNum == 1) || ((PageNum == 2) && (Speed == 1)))
            {
            PutWaveFormIntoSlice( PageNum,col,res,Slice,Speed );
            AddGrid( Slice,col,res,Site );
            }
}
```

```
/* ::PL -ey -ry */
/**************************************************************

$Logfile:    I:/quarry/fax/vcs/qscfxb15.c_v    $

FILE NAME: QSCFXB15.C          MODULE: CopyOverlap

SYSTEM: FAX
    SUBSYSTEM: Build Slice (C) COPYRIGHT HEWLETT-PACKARD COMPANY 1989
            All rights reserved

************* HP CONFIDENTIAL **************

$Date:    12 Jun 1992 13:30:34  $ $Revision:   1.2  $

NOTES:    C Source file
              Created by Lawrence Hileman
    ----------------------------------------------------------
    ORIGIN:   Cardiology Business Unit REVISIONS:
    $Log:    I:/quarry/fax/vcs/qscfxb15.c_v   $
**
**      Rev 1.2    12 Jun 1992 13:30:34    Larry_H
** add 300 DPI
**
**      Rev 1.0    07 Aug 1991 21:32:28    Larry_H
** Initial revision.

***************************************************************/ include        "qpcfxint.h"     /* Fax prototypes              */
include        "qecfx010.h"     /* FAX resolutions and report types */ include        "QTCFXV00.H"     /* slice defined */

/* check point access */
#include        "QECLSJWL.H"     /* #define check point values */
include        "qvcls02d.h"     /* extern unsigned short check_point */ void CopyOverlap( Fsl, lastcol )
struct  SLICE   *Fsl;
int lastcol;
{
        check_point= FAX_COPY_COL_17_TO_0;

Fsl->SliceCol[ 0]=Fsl->SliceCol[lastcol]   ;    /* copy 17 into 1 */
        Fsl->SliceCol[ 1]=Fsl->SliceCol[lastcol+1];     /* copy 17 into 1 */
        Fsl->SliceCol[lastcol]   =Fsl->SliceCol[ 2];    /* copy cleared 2 to 17 */
        Fsl->SliceCol[lastcol+1]=Fsl->SliceCol[ 2];     /* copy cleared 2 to 17 */
}
```

```
/* ::PL -ey -ry */
/*************************************************************

$Logfile:   I:/quarry/fax/vcs/qscfxb20.c_v  $

FILE NAME: QSCFXB20.C        MODULE: ClearSlice

SYSTEM: FAX
    SUBSYSTEM: Build Slice (C) COPYRIGHT HEWLETT-PACKARD COMPANY 1989
               All rights reserved

************** HP CONFIDENTIAL **************

$Date:    12 Jun 1992 13:33:24  $ $Revision:   1.2  $

NOTES:    C Source file
              Created by Lawrence Hileman
---------------------------------------------------------------
    ORIGIN:   Cardiology Business Unit REVISIONS:
    $Log:   I:/quarry/fax/vcs/qscfxb20.c_v  $
**
**     Rev 1.2   12 Jun 1992 13:33:24   Larry_H
** add 300 DPI
**
**     Rev 1.1   29 May 1992 12:20:16   Larry_H
** add slice size
**
**     Rev 1.0   07 Aug 1991 21:32:54   Larry_H
** Initial revision.

*************************************************************/ include        "qpcfxint.h"    /* Fax prototypes              */
include        "qecfx010.h"    /* FAX resolutions and report types */ include        "QTCFXV00.H"    /* slice defined */

/* check point access */
#include        "QECLSJWL.H"    /* #define check point values */
include        "qvcls02d.h"    /* extern unsigned short check_point */ void ClearSlice( slc,col )
struct SLICE *slc;
int col;
{
        int i,j,k;
        check_point= FAX_CLEAR_SLICE;
        k=LENGTH_OF_LINE_300/4;
        for (i=0;i<k;i++)
                for (j=0;j<col;j++)
                        slc->SliceCol[j].LIntData[i]=0;
}
```

```
/* ::PL -ey -ry */
/************************************************************

$Logfile:   I:/quarry/fax/vcs/qscfxb30.c_v $

FILE NAME: QSCFXB30.C          MODULE: PutTextIntoSlice

SYSTEM: FAX
    SUBSYSTEM: Build Slice (C) COPYRIGHT HEWLETT-PACKARD COMPANY 1989
                All rights reserved

************* HP CONFIDENTIAL **************

$Date:    21 Jul 1992 13:03:20 $ $Revision:   1.8  $

NOTES:    C Source file
              Created by Lawrence Hileman
    ------------------------------------------------------------
    ORIGIN:   Cardiology Business Unit REVISIONS:
    $Log:    I:/quarry/fax/vcs/qscfxb30.c_v $
**
**     Rev 1.8    21 Jul 1992 13:03:20    Larry_H
** remove unneeded include file
**
**     Rev 1.7    12 Jun 1992 15:34:46    Larry_H
** resolution mismatch, ok now
**
**     Rev 1.6    12 Jun 1992 14:08:44    Larry_H
** OOOOPS!!! into instead of in, ratts
**
**     Rev 1.5    12 Jun 1992 13:27:34    Larry_H
** added 300 DPI
**
**     Rev 1.4    29 May 1992 12:20:54    Larry_H
** add slice size
**
**     Rev 1.3    19 Nov 1991 10:49:46    Larry_H
** on 50mm/sec ECGs, do the filter box on the second page
**
**     Rev 1.2    25 Sep 1991 18:41:44    Larry_H
** remove bottom line, it just has garbage in it!!
**
**     Rev 1.1    08 Aug 1991 11:03:52    Larry_H
** fix problem with filter box
**
**     Rev 1.0    07 Aug 1991 21:33:26    Larry_H
** Initial revision.

*************************************************************/ include      "qpcfxint.h"    /* Fax prototypes                  */ include      "QECW9006.H"    /* defines for pr_text_block */
include      "QVCW9006.H"    /* extern for pr_text_block */
```

```
#include         "QECFX010.H"     /* slice size defined */
include         "QTCFXV00.H"     /* slice defined */ include         "qeclh005.h"     /* Config defines              */
include         "qtclh005.h"     /* Config structure defines    */
include         "qvclh005.h"     /* Config variable defines     */ include         "eeclj023.l"     /* Font Defines */
include         "etclj023.h"     /* Font Structure */
#include         "evclj023.h"     /* Font Extern */

/* check point access */
#include         "QECLSJWL.H"     /* #define check point values */
include         "qvcls02d.h"     /* extern unsigned short check_point */ static void PutTextIntoSlice200( int, struct SLICE * );
static void PutTextIntoSlice300( int, struct SLICE * );

void PutTextIntoSlice( col, res, Slice )
struct SLICE *Slice;
int col,res;
{
        if (res == SIZE_FOR_300_RESOLUTION)
                PutTextIntoSlice300( col, Slice );
            else
                PutTextIntoSlice200( col, Slice );
} static void OrSliceValue( Slice, Col, Row, Byte )
struct SLICE *Slice;
int Col,Row;
unsigned char Byte;
{
        if ((Col < 0) || (Col >= COLUMNS_PER_SLICE_300))       return;
        if ((Row < 0) || (Row >= LENGTH_OF_LINE_300))          return;

Slice->SliceCol[ Col ].CharData[ Row ]|=Byte;
} static void PutTextIntoSlice200( col, Slice )
struct SLICE *Slice;
int col;
{
        unsigned char c,f,n;
        unsigned int i,j,k,row;
        int LLcol,LRcol;

check_point= FAX_PUT_TEXT_INTO_SLICE;

LLcol=LRcol=0;
        if (config.prt_interp.value == CONFIG_PRT_EXT_MM)
                {LLcol=90;LRcol=109;}
            else
                if (col < 110)  {LLcol= 89;LRcol=108;}
                    else        {LLcol=221;LRcol=240;} for (i=0;i<PR_MAX_LINES;i++)    /* all rows for this column */
            {
            c=(unsigned char) pr_text_block[i][col];
```

```
switch (c)
    {
    case 0xB3:      /* vertical bar */
            c=' ';
            Slice->SliceCol[ 8].LIntData[51-i]=0xffffffff;
            Slice->SliceCol[ 9].LIntData[51-i]=0xffffffff;
            if (i == 50)
                {
                if (col == LLcol)
                    for (j=10;j<16;j++)
                            Slice->SliceCol[j].LIntData[1]=0x000000C
                if (col == LRcol)
                    for (j=0;j<8;j++)
                            Slice->SliceCol[j].LIntData[1]=0x000000C
                }
            break;
    case 0xC4:      /* horizontal bar */
            c=' ';
            for (j=0;j<16;j++)
                    Slice->SliceCol[j].LIntData[51-i]=0x00800100;
            break;
    case 0xBF:      /* upper right */
            c=' ';
            Slice->SliceCol[ 8].LIntData[51-i]=0x0080ffff;
            Slice->SliceCol[ 9].LIntData[51-i]=0x0000ffff;
            for (j=0;j<8;j++)
                    Slice->SliceCol[j].LIntData[51-i]=0x00800100;
            break;
    case 0xDA:      /* upper left */
            c=' ';
            Slice->SliceCol[ 8].LIntData[51-i]=0x0000ffff;
            Slice->SliceCol[ 9].LIntData[51-i]=0x0080ffff;
            for (j=10;j<16;j++)
                    Slice->SliceCol[j].LIntData[51-i]=0x00800100;
            break;
    case 0xD9:      /* lower right */
            c=' ';
            Slice->SliceCol[ 8].LIntData[51-i]=0xffff0100;
            Slice->SliceCol[ 9].LIntData[51-i]=0xffff0000;
            for (j=0;j<8;j++)
                    Slice->SliceCol[j].LIntData[51-i]=0x00800100;
            break;
    case 0xC0:      /* lower left */
            c=' ';
            Slice->SliceCol[ 8].LIntData[51-i]=0xffff0000;
            Slice->SliceCol[ 9].LIntData[51-i]=0xffff0100;
            for (j=10;j<16;j++)
                    Slice->SliceCol[j].LIntData[51-i]=0x00800100;
            break;
    } for (j=0;j<11;j++)
    {
    f=~((unsigned char)font[c].char_row[j]);
    for (k=0;k<8;k++)
            {
            row=((51-i)*4+(3-(j>>2)));
            n=((f&(0x80>>k))>>(7-k)) << (2*(j&3));
            Slice->SliceCol[k*2  ].CharData[row]|=n;
```

```
                            Slice->SliceCol[k*2  ].CharData[row]|=n<<1;
                            Slice->SliceCol[k*2+1].CharData[row]|=n;
                            Slice->SliceCol[k*2+1].CharData[row]|=n<<1;
                            }
                }
        }

/* add lower part of filter box */
        if ((col > LLcol) && (col < LRcol))
                for (j=0;j<16;j++)
                        Slice->SliceCol[j].CharData[4]|=0xC0;

/* add seperator line for banner */
        if (col < 122)
                for (i=0;i<16;i++)
                        {
                        Slice->SliceCol[i].CharData[204]|=0x07;
                        Slice->SliceCol[i].CharData[205]|=0x80;
                        }
} static void PutTextIntoSlice300( col, Slice )
struct SLICE *Slice;
int col;
{
        unsigned char c,f,b;
        unsigned int i,j,k,l,n,row,r;
        int LLcol,LRcol;

check_point= FAX_PUT_TEXT_INTO_SLICE;

LLcol=LRcol=0;
        if (config.prt_interp.value == CONFIG_PRT_EXT_MM)
                {LLcol=90;LRcol=109;}
            else
                if (col < 110)  {LLcol= 89;LRcol=108;}
                    else        {LLcol=221;LRcol=240;} for (i=0;i<PR_MAX_LINES;i++)    /* all rows for this column */
                {
                c=(unsigned char) pr_text_block[i][col];

row= (49-i)*6+1;

switch (c)
                        {
                        case 0xB3:      /* vertical bar */
                                c=' ';
                                for (k=0;k<6;k++)
                                        {
                                        OrSliceValue( Slice, 10, row+k, 0xff);
                                        OrSliceValue( Slice, 11, row+k, 0xff);
                                        OrSliceValue( Slice, 12, row+k, 0xff);
                                        }
                                break;
                        case 0xC4:      /* horizontal bar */
                                c=' ';
                                for (j=0;j<COLUMNS_PER_SLICE_300;j++)
                                        {
```

```
                        OrSliceValue( Slice, j, row+2, 0x03);
                        OrSliceValue( Slice, j, row+3, 0x80);
                        }
            break;
case 0xBF:      /* upper right */
        c=' ';
        OrSliceValue( Slice, 10, row  , 0xff);
        OrSliceValue( Slice, 10, row+1, 0xff);
        OrSliceValue( Slice, 10, row+2, 0xff);
        OrSliceValue( Slice, 11, row  , 0xff);
        OrSliceValue( Slice, 11, row+1, 0xff);
        OrSliceValue( Slice, 11, row+2, 0xff);
        OrSliceValue( Slice, 12, row  , 0xff);
        OrSliceValue( Slice, 12, row+1, 0xff);
        OrSliceValue( Slice, 12, row+2, 0xff);
        for (j=0;j<11;j++)
                {
                OrSliceValue( Slice, j, row+2, 0x03);
                OrSliceValue( Slice, j, row+3, 0x80);
                }
        break;
case 0xDA:      /* upper left */
        c=' ';
        OrSliceValue( Slice, 10, row  , 0xff);
        OrSliceValue( Slice, 10, row+1, 0xff);
        OrSliceValue( Slice, 10, row+2, 0xff);
        OrSliceValue( Slice, 11, row  , 0xff);
        OrSliceValue( Slice, 11, row+1, 0xff);
        OrSliceValue( Slice, 11, row+2, 0xff);
        OrSliceValue( Slice, 12, row  , 0xff);
        OrSliceValue( Slice, 12, row+1, 0xff);
        OrSliceValue( Slice, 12, row+2, 0xff);
        for (j=11;j<COLUMNS_PER_SLICE_300;j++)
                {
                OrSliceValue( Slice, j, row+2, 0x03);
                OrSliceValue( Slice, j, row+3, 0x80);
                }
        break;
case 0xD9:      /* lower right */
        c=' ';
        OrSliceValue( Slice, 10, row+3, 0xff);
        OrSliceValue( Slice, 10, row+4, 0xff);
        OrSliceValue( Slice, 10, row+5, 0xff);
        OrSliceValue( Slice, 11, row+3, 0xff);
        OrSliceValue( Slice, 11, row+4, 0xff);
        OrSliceValue( Slice, 11, row+5, 0xff);
        OrSliceValue( Slice, 12, row+3, 0xff);
        OrSliceValue( Slice, 12, row+4, 0xff);
        OrSliceValue( Slice, 12, row+5, 0xff);
        for (j=0;j<11;j++)
                {
                OrSliceValue( Slice, j, row+2, 0x03);
                OrSliceValue( Slice, j, row+3, 0x80);
                }
        break;
case 0xC0:      /* lower left */
        c=' ';
        OrSliceValue( Slice, 10, row+3, 0xff);
        OrSliceValue( Slice, 10, row+4, 0xff);
        OrSliceValue( Slice, 10, row+5, 0xff);
```

```
                    OrSliceValue( Slice, 11, row+3, 0xff);
                    OrSliceValue( Slice, 11, row+4, 0xff);
                    OrSliceValue( Slice, 11, row+5, 0xff);
                    OrSliceValue( Slice, 12, row+3, 0xff);
                    OrSliceValue( Slice, 12, row+4, 0xff);
                    OrSliceValue( Slice, 12, row+5, 0xff);
                    for (j=11;j<COLUMNS_PER_SLICE_300;j++)
                        {
                            OrSliceValue( Slice, j, row+2, 0x03);
                            OrSliceValue( Slice, j, row+3, 0x80);
                        }
                    break;
            } for (k=0;k<8;k++)
            {
            for (j=0;j<33;j++)
                    {
                    l=j/3;
                    f=~((unsigned char)font[c].char_row[l]);
                    r=(32-j)/8;
                    n=(32-j)-(r*8);
                    b=((f&(0x80>>k)) >> (7-k));
                    if (b == 0)     continue;
                    OrSliceValue( Slice, k*3  , row+r, (0x80>>n));
                    OrSliceValue( Slice, k*3+1, row+r, (0x80>>n));
                    OrSliceValue( Slice, k*3+2, row+r, (0x80>>n));
                    }
            }

/* add lower part of filter box */
    if ((col > LLcol) && (col < LRcol))
            for (j=0;j<COLUMNS_PER_SLICE_300;j++)
                    OrSliceValue( Slice, j, 0, 0xE0);
    if (col == LLcol)
            for (j=11;j<COLUMNS_PER_SLICE_300;j++)
                    OrSliceValue( Slice, j, 0, 0xE0);
    if (col == LRcol)
            for (j=0;j<11;j++)
                    OrSliceValue( Slice, j, 0, 0xE0);

}
```

```
/* ::PL -ey -ry */
/***********************************************************

$Logfile:   I:/quarry/fax/vcs/qscfxb40.c_v  $

FILE NAME: QSCFXB40.C          MODULE: Add Lead Seperators

SYSTEM: FAX
    SUBSYSTEM: Build Slice (C) COPYRIGHT HEWLETT-PACKARD COMPANY 1989
              All rights reserved

************** HP CONFIDENTIAL **************

$Date:    21 Jul 1992 13:04:28  $ $Revision:   1.2  $

NOTES:   C Source file
             Created by Lawrence Hileman
---------------------------------------------------------
    ORIGIN:  Cardiology Business Unit REVISIONS:
    $Log:    I:/quarry/fax/vcs/qscfxb40.c_v  $
**
**    Rev 1.2   21 Jul 1992 13:04:28    Larry_H
** remove unneeded include file
**
**    Rev 1.1   12 Jun 1992 13:34:40    Larry_H
** add 300 DPI
**
**    Rev 1.0   07 Aug 1991 21:33:50    Larry_H
** Initial revision.

***********************************************************/ include       "qpcfxint.h"     /* Fax prototypes               */
include       "qecfx010.h"     /* FAX resolutions and report types */ include       "QTCFXV00.H"     /* slice defined */

/* check point access */
#include       "QECLSJWL.H"     /* #define check point values */
include       "qvcls02d.h"     /* extern unsigned short check_point */ void AddLeadSep( NewSam, OldSam, Slice0, Slice1 )
int NewSam;
int OldSam;
char *Slice0,*Slice1;
{
        int i,min,max;

check_point= FAX_ADD_LEAD_SEP;

if (NewSam < OldSam)
               {
               min=NewSam;
               max=OldSam;
```

```
            }
    else
        {
        min=OldSam;
        max=NewSam;
        } min-=45;
max+=10;

for (i=0;i<35;i++)
        {
        PutDot( Slice0 , min+i , WAVEFORM_HEIGHT_300 );
        PutDot( Slice0 , max+i , WAVEFORM_HEIGHT_300 );
        PutDot( Slice1 , min+i , WAVEFORM_HEIGHT_300 );
        PutDot( Slice1 , max+i , WAVEFORM_HEIGHT_300 );
        }
}
```

```
/* ::PL -ey -ry */
/***********************************************************

$Logfile:    I:/quarry/fax/vcs/qscfxb50.c_v   $

FILE NAME: QSCFXB50.C           MODULE: PutWaveformIntoSlice

SYSTEM: FAX
    SUBSYSTEM: Build Slice (C) COPYRIGHT HEWLETT-PACKARD COMPANY 1989
                 All rights reserved

************** HP CONFIDENTIAL **************

$Date:    24 Jul 1992 09:01:18   $ $Revision:   1.5  $

NOTES:    C Source file
              Created by Lawrence Hileman
    ----------------------------------------------------------
    ORIGIN:   Cardiology Business Unit REVISIONS:
    $Log:    I:/quarry/fax/vcs/qscfxb50.c_v    $
**
**    Rev 1.5   24 Jul 1992 09:01:18   Larry_H
** if the size is zero, don't print the line to the next point
**
**    Rev 1.4   26 Jun 1992 14:38:02   Larry_H
** fix for laser jet printing
**
**    Rev 1.3   12 Jun 1992 13:37:36   Larry_H
** add 300 DPI
**
**    Rev 1.2   04 Feb 1992 19:55:04   Larry_H
** if we have finished with this line of ECG, don't print another 16 columns
** of it
**
**    Rev 1.1   28 Jan 1992 08:51:56   Larry_H
** fix transmission problem with A.01 6x2 ecgs
**
**    Rev 1.0   07 Aug 1991 21:34:26   Larry_H
** Initial revision.

************************************************************/ include       "QECLS01U.H"       /* TRUE */
include       "QECLS01V.H"       /* FALSE */ include       "qeclh014.h"       /* 11 second structure defines (NUM_11SEC_ENTRIE
include       "qtclh013.h"       /* 11 second uncompressed ECG data struct*/
include       "qvclh013.h"       /* 11 second uncompressed ECG variabel  */ include       "qecls04h.h"       /* ec_extension defines            */
include       "qtcls04h.h"       /* ec_extension structure          */
include       "qvcls04h.h"       /* ec_extension variable           */ include       "qeclh005.h"       /* config defines         */
```

```c
#include        "qeci0007.h"    /* ID Header stuff            */
#include        "qtclh015.h"    /* ID Header structure        */
include        "qvclh015.h"    /* ID Header variable         */ include        "QECFX010.H"    /* SIZE_FOR_COURSE_RESOLUTION */
include        "QECFXB50.H"    /* Dot Types */ include        "QTCFXV00.H"    /* Slice define */ include        "QVCFXV40.H"    /* LeadOrgs */
include        "QVCFXV50.H"    /* LeadToPrint */ include        "qpcfxint.h"    /* Fax prototypes             */

/* check point access */
#include        "QECLSJWL.H"    /* #define check point values */
include        "qvcls02d.h"    /* extern unsigned short check_point */
void PutWaveFormIntoSlice( pagenum,col,res,Slice,Speed )
int pagenum,col,res,Speed;
struct SLICE *Slice;
{
        int point,nextpoint;
        int i,j,k,num,ltp,delta,Limit,ColPerSlc;
        static int index[6];
        static int lead[6],size[6];
        static int ltpp,config,OldSam[6];

check_point= FAX_PUT_WAVEFORM_INTO_SLICE;

if (col == 0)   /* Initialize */
                {
                config = (int)ec_extension.ecg_format;
                if (pagenum == 1)       ltpp=Speed;
                        else            ltpp=2;
                for (i=0;i<6;i++)
                        {
                        index[i]= 1;
                        lead[i]= 0;
                        ltp=LeadToPrint[ltpp][config][i][lead[i]];
                        size[i]= *wfcom_.ecg.lead[ltp];
                        OldSam[i]=LeadOrgs[config][i];
                        if (res == SIZE_FOR_300_RESOLUTION)
                                OldSam[i]+= OldSam[i]/2;
                        }
                } switch(res)
                {
                case SIZE_FOR_COURSE_RESOLUTION:
                        num=2;ColPerSlc=COLUMNS_PER_SLICE;Limit=WAVEFORM_HEIGHT;
                        break;
                case SIZE_FOR_FINE_RESOLUTION:
                        num=1;ColPerSlc=COLUMNS_PER_SLICE;Limit=WAVEFORM_HEIGHT;
                        break;
                case SIZE_FOR_300_RESOLUTION:
                        num=1;ColPerSlc=COLUMNS_PER_SLICE_300;Limit=WAVEFORM_HEI
                        break;
                }
```

```
for (i=0;i<6;i++)
    {
    if (LeadOrgs[config][i] == -1)                      continue;
    if (LeadToPrint[ltpp][config][i][lead[i]] == -1)    continue;

for (j=0;j<ColPerSlc;j+=num)
        {
        ltp=LeadToPrint[ltpp][config][i][lead[i]];
        if (size[i] == 0)
            {
            lead[i]++;
            index[i]=1;
            ltp=LeadToPrint[ltpp][config][i][lead[i]];
            size[i]=*wfcom_.ecg.lead[ltp];
            nextpoint = ((wfcom_.ecg.lead[ltp][1])*4)/10;
            nextpoint+= LeadOrgs[config][i];
            if (res == SIZE_FOR_300_RESOLUTION)
                    nextpoint+= nextpoint/2;
            if (ltp == -1)
                    break;
            AddLeadSep( nextpoint,OldSam[i],Slice->SliceCol[j].CharD
                                          ,Slice->SliceCol[j+1].Ch
            if (nextpoint > OldSam[i])
                    {
                    delta=(nextpoint-OldSam[i])/2;
                    for (k=1;k<=delta;k++)
                            PutWFDot( Slice,j,OldSam[i]+k,Limit );
                    }
            if (nextpoint < OldSam[i])
                    {
                    delta=(OldSam[i]-nextpoint+1)/2;
                    for (k=1;k<delta;k++)
                            PutWFDot( Slice,j,OldSam[i]-k,Limit );
                    }
            } size[i]--;

point = LeadOrgs[config][i] +
                ((wfcom_.ecg.lead[ltp][index[i]++])*4)/10;
        if (res == SIZE_FOR_300_RESOLUTION)
                point+= point/2;

PutWFDot( Slice,j,point,Limit );
        if (point > OldSam[i])
                {
                delta=(point-OldSam[i])/2;
                for (k=1;k<=delta;k++)
                        PutWFDot( Slice,j,point-k,Limit );
                }
        if (point < OldSam[i])
                {
                delta=(OldSam[i]-point+1)/2;
                for (k=1;k<delta;k++)
                        PutWFDot( Slice,j,point+k,Limit );
                }

OldSam[i]=point;
```

```
        if (size[i] == 0)       continue;

nextpoint = LeadOrgs[config][i] +
            ((wfcom_.ecg.lead[ltp][index[i]])*4)/10;
if (res == SIZE_FOR_300_RESOLUTION)
        nextpoint+= nextpoint/2;
if (point > nextpoint)
        {
        delta=(point-nextpoint)/2;
        for (k=1;k<=delta;k++)
                PutWFDot( Slice,j,point-k,Limit );
        }
if (point < nextpoint)
        {
        delta=(nextpoint-point+1)/2;
        for (k=1;k<delta;k++)
                PutWFDot( Slice,j,point+k,Limit );
        }
    }
  }
}
```

```
;***********************************************************
;
;    $Logfile:   I:/quarry/fax/vcs/qsafxb60.asv  $
;
;    FILE NAME: QSAFXB600.ASM          MODULE: Put Dot
;
;    SYSTEM: FAX
;    SUBSYSTEM: Main
;
;    (C) COPYRIGHT HEWLETT-PACKARD COMPANY 1989
;                 All rights reserved
;
;    ************* HP CONFIDENTIAL **************
;
;    $Date:    12 Jun 1992 13:43:16  $
;
;    $Revision:   1.1  $
;
;    NOTES:   Asm Source file
;             Created by Lawrence Hileman
;-----------------------------------------------------------
;    ORIGIN:   Cardiology Business Unit
;
;    REVISIONS:
;    $Log:   I:/quarry/fax/vcs/qsafxb60.asv  $
;
;       Rev 1.1   12 Jun 1992 13:43:16    Larry_H
;    add 300 DPI
;
;       Rev 1.0   07 Aug 1991 21:34:38    Larry_H
;    Initial revision.
;
;***********************************************************/
        assume  cs:codeseg
        assume  ds:dataseg
dataseg         segment dword rw use32 public 'data'
extrn           _check_point:DWORD
dataseg         ends BYTES_PER_SLICECOL      equ     324 codeseg         segment dword er use32 public 'code'
                public  _PutDot
                align   4

;void PutDot( str, Index, Limit )
;char *str;
;int Index,Limit;
;{
;       register int data,byte,cnt;
;
;       check_point= FAX_PUT_DOT;
;
;       cnt=Index;
;       if (cnt < 1)            return;
;       if (cnt > Limit)        return;
;
;       data=0x80 >> (cnt&0x07);
;       cnt=cnt>>3;
```

```
;         str[cnt]|=(char) data;
;
;         check_point= FAX_PUT_DOT;
;}

_PutDot         proc    near push    ebp
                mov     ebp,esp
                push    ebx
                push    ecx
                push    edi mov     word ptr ds:_check_point, 1F2bh mov     ecx,dword ptr [ebp+12]
                cmp     ecx,1
                jl      PutDotEnd
                cmp     ecx,[ebp+16]
                jg      PutDotEnd mov     ebx,ecx
                shr     ebx,3
                and     ecx,07h
                mov     al,80h
                shr     al,cl mov     edi,[ebp+8]
                or      byte ptr [edi+ebx],al PutDotEnd:
                mov     word ptr ds:_check_point, 1F2bh pop     edi
                pop     ecx
                pop     ebx
                pop     ebp ret _PutDot         endp
codeseg         ends
                end
```

```
        PutDot( Slice->SliceCol[Col+1].CharData, Index+i, Limit );
    }
}
```

```
/* ::PL -ey -ry */
/************************************************************

$Logfile:    I:/quarry/fax/vcs/qscfxb70.c_v  $

FILE NAME: QSCFXB70.C          MODULE: AddGrid

SYSTEM: FAX
    SUBSYSTEM: Build Slice (C) COPYRIGHT HEWLETT-PACKARD COMPANY 1989
             All rights reserved

************** HP CONFIDENTIAL **************

$Date:     24 Jul 1992 10:31:36  $ $Revision:  1.5  $

NOTES:   C Source file
             Created by Lawrence Hileman
----------------------------------------------------------------
    ORIGIN:  Cardiology Business Unit REVISIONS:
    $Log:   I:/quarry/fax/vcs/qscfxb70.c_v  $
**
**     Rev 1.5   24 Jul 1992 10:31:36   Larry_H
** remove log_errors
**
**     Rev 1.4   24 Jul 1992 09:40:58   Larry_H
** mix real and false grid, add partial real grid to false grid
**
**     Rev 1.3   20 Jun 1992 00:15:40   Larry_H
** add low grid option
**
**     Rev 1.2   12 Jun 1992 13:40:20   Larry_H
** add 300 DPI
**
**     Rev 1.1   19 Nov 1991 10:51:00   Larry_H
** when doing a 50mm/sec ECG, do 255 slices completely, then 2 columns in
** slice 256
**
**     Rev 1.0   07 Aug 1991 21:35:34   Larry_H
** Initial revision.

************************************************************/ include       "QECFX010.H"     /* SIZE_FOR_COURSE_RESOLUTION */ include       "QECFXV60.H"     /* GRID_START */
include       "QVCFXV60.H"     /* GridCols */ include       "qeclh005.h"     /* Config defines          */
include       "qtclh005.h"     /* Config structure        */
include       "qvclh005.h"     /* Config variable         */ include       "qeci0007.h"     /* ID Header stuff         */
include       "qtclh015.h"     /* ID Header structure     */
#include       "qvclh015.h"     /* ID Header variable      */
```

```
/* ::PL -ey -ry */
/*************************************************************

$Logfile:    I:/quarry/fax/vcs/qscfxb65.c_v  $

FILE NAME: QSCFXB65.C           MODULE: PutWFDot

SYSTEM: FAX
    SUBSYSTEM: Build Slice (C) COPYRIGHT HEWLETT-PACKARD COMPANY 1989
              All rights reserved

************** HP CONFIDENTIAL **************

$Date:    21 Jul 1992 13:06:14   $ $Revision:    1.2  $

NOTES:    C Source file
              Created by Lawrence Hileman
-----------------------------------------------------------
    ORIGIN: Cardiology Business Unit REVISIONS:
    $Log:    I:/quarry/fax/vcs/qscfxb65.c_v  $
**
**    Rev 1.2    21 Jul 1992 13:06:14    Larry_H
** remove unneeded include file
**
**    Rev 1.1    12 Jun 1992 13:38:52    Larry_H
** add 300 DPI
**
**    Rev 1.0    07 Aug 1991 21:35:06    Larry_H
** Initial revision.

**************************************************************/ include        "QECFXB50.H"    /* Dot Types */
include        "qecfx010.h"    /* FAX resolutions and report types */ include        "QTCFXV00.H"    /* slice defined */ include        "qpcfxint.h"    /* Fax prototypes                  */

/* check point access */
#include        "QECLSJWL.H"    /* #define check point values */
include        "qvcls02d.h"    /* extern unsigned short check_point */ void PutWFDot( Slice, Col, Index, Limit )
struct SLICE *Slice;
int Col,Index,Limit;
{
        int i;

check_point= FAX_PUT_WF_DOT;

for (i=0;i<3;i++)
                {
                PutDot( Slice->SliceCol[Col+i].CharData, Index+1, Limit );
```

```
#include         "QTCFXV00.H"    /* slice defined */
#include         "qpcfxint.h"    /* Fax prototypes                  */

/* check point access */
#include         "QECLSJWL.H"    /* #define check point values */
include         "qvcls02d.h"    /* extern unsigned short check_point */ void AddGrid( Slice,col,res,Site )
struct SLICE *Slice;
int col,res,Site;
{
        static short int TrueOnFalse;

int i,j,row,k,l,m,Limit,size,rep;
        int G5m,G1m,Ghm,Gs,Ge;

check_point= FAX_ADD_GRID;

if (col == 0)    TrueOnFalse=FALSE_5MM_H;

i=config.connection[Site].grid_on.value;

if (i == CONFIG_GRID_ON)
              {
                switch(res)             /* Real Grid */
                  {
                   case SIZE_FOR_COURSE_RESOLUTION:
                          l=0;size=COLUMNS_PER_SLICE;rep=77;Limit=WAVEFORM
                          G5m=4;Ghm=40;G1m=8;Gs=GRID_START;Ge=GRID_END;
                          break;
                   case SIZE_FOR_FINE_RESOLUTION:
                          l=1;size=COLUMNS_PER_SLICE;rep=77;Limit=WAVEFORM
                          G5m=4;Ghm=40;G1m=8;Gs=GRID_START;Ge=GRID_END;
                          break;
                   case SIZE_FOR_300_RESOLUTION:
                          l=2;size=COLUMNS_PER_SLICE_300;rep=59;Limit=WAVE
                          G5m=6;Ghm=60;G1m=12;Gs=GRID_START_300;Ge=GRID_EN
                          break;
                  }
              }
        else
              {
                switch(res)             /* False Grid */
                  {
                   case SIZE_FOR_COURSE_RESOLUTION:
                          l=3;size=COLUMNS_PER_SLICE;rep=77;Limit=WAVEFORM
                          G5m=40;Ghm=40;G1m=8;Gs=GRID_START;Ge=GRID_END;
                          break;
                   case SIZE_FOR_FINE_RESOLUTION:
                          l=4;size=COLUMNS_PER_SLICE;rep=77;Limit=WAVEFORM
                          G5m=40;Ghm=40;G1m=8;Gs=GRID_START;Ge=GRID_END;
                          break;
                   case SIZE_FOR_300_RESOLUTION:
                          l=5;size=COLUMNS_PER_SLICE_300;rep=59;Limit=WAVE
                          G5m=60;Ghm=60;G1m=12;Gs=GRID_START_300;Ge=GRID_E
                          break;
                  }
              }
```

```
            m=size;
/*          if (id_header.plotting_speed[0] == '1') / 50mm/sec /
                    (if (col == 256)        m=2;)
                else
                    (if (col == 127)        m=11;}*/ for (i=0;i<m;i++)
                {
                row=((col*size)+i)%rep;
                for (j=-1,k=0;GridCols[l%3][k][0] != -1;k++)
                    {
                    if (GridCols[l%3][k][0] == row)
                        {j=GridCols[l%3][k][1];break;}
                    }
                if (j == -1)    continue;       /* no grid on this line */ switch(j){
                    case GRID_5MM:
                        if (l > 2)
                            {
                            if (TrueOnFalse != 0)
                                {
                                for (k=0;k<=Glm*FALSE_MM_V;k+=Ghm/10)
                                    PutDot( Slice->SliceCol[i].CharD
                                }
                            }
                        for (k=Gs;k<=Ge;k+=G5m)
                            {
                            PutDot( Slice->SliceCol[i].CharData,k,Li
                            }
                        for (k=Gs+1 ;k<=Ge;k+=Ghm)
                            PutDot( Slice->SliceCol[i].CharData,k,Li
                        for (k=Gs+Ghm-1;k<=Ge;k+=Ghm)
                            PutDot( Slice->SliceCol[i].CharData,k,Li
                        if (TrueOnFalse > 0)    TrueOnFalse--;
                        break;
                    case GRID_F1MM:
                        if (l > 2)
                            {
                            if (TrueOnFalse != 0)
                                {
                                for (k=0;k<=Glm*FALSE_MM_V;k+=Glm)
                                    PutDot( Slice->SliceCol[i].CharD
                                }
                            break;
                            }
                    case GRID_1MM:
                        for (k=Gs;k<=Ge;k+=Glm)
                            PutDot( Slice->SliceCol[i].CharData,k,Li
                        break;
                    case GRID_FHMM:
                        if (l > 2)
                            {
                            if (TrueOnFalse != 0)
                                {
                                for (k=0;k<=Ghm*(FALSE_MM_V/5);k+=Ghm)
                                    PutDot( Slice->SliceCol[i].CharD
                                }
                            break;
                            }
```

```
        case GRID_HMM:
            for (k=Gs;k<=Ge;k+=Ghm)
                    PutDot( Slice->SliceCol[i].CharData,k,Li
            break;

}
}
}
```

```
/* ::PL -ey
/******************************************************

$Logfile:   I:/quarry/fax/vcs/qscfxs30.c_v  $

FILE NAME: QSCFXS30.C        MODULE: Encode Strip In Slice

SYSTEM: FAX
    SUBSYSTEM: Send Slice (C) COPYRIGHT HEWLETT-PACKARD COMPANY 1989
                All rights reserved

************** HP CONFIDENTIAL **************

$Date:   29 May 1992 12:22:06  $ $Revision:   1.1  $

NOTES:   C Source file
             Created by Lawrence Hileman
    --------------------------------------------------
    ORIGIN:  Cardiology Business Unit REVISIONS:
    $Log:   I:/quarry/fax/vcs/qscfxs30.c_v  $
**
**     Rev 1.1    29 May 1992 12:22:06   Larry_H
** add slice size
**
**     Rev 1.0    07 Aug 1991 21:38:10   Larry_H
** Initial revision.

*********************************************************/ include       "QECFXS40.H"     /* Define Line_Length */ include       "qpcfxint.h"     /* Fax prototypes                */ include       "QECFX010.H"     /* slice size defined */
include       "QTCFXV00.H"     /* structure for slice */
#include       "QVCFXV10.H"     /* termiate and makeup codes */

/* check point access */
#include       "QECLSJWL.H"              /* #define check point values */
include       "qvcls02d.h"              /* extern unsigned short check_point */ void EncodeStripInSlice( Colum, OutMsg, col, oind )
union SLICE_ROW *Colum;
unsigned char *OutMsg;
int col;
unsigned int *oind;
{
        int value,index,newind,delta,i;

check_point= FAX_ENCODE_STRIP_IN_SLICE;

if (col != 0)
                AddCodeToOutput( OutMsg,oind,MakeUpCode[0][40] );    /* EOL */
```

```
for (index=0,newind=0,value=0;index<LINE_LENGTH;value=(value+1)&0x01)
    {
    newind=NextMatch( Colum->CharData, index, value );
    delta=newind-index;
    if (delta > 63)
                            /* add make-up code */
            {
            i=(delta/64)-1; /* number of 64's */
            AddCodeToOutput( OutMsg,oind,MakeUpCode[value][i] );
            delta=delta&0x3f;
            }
    AddCodeToOutput( OutMsg,oind,TermCode[value][delta] );
    index=newind;
    }
}
```

```
;***************************************************************
;
;       $Logfile:   I:/quarry/fax/vcs/qsafxs40.asv  $
;
;       FILE NAME: QSAFXS40.ASM           MODULE: Add Code to output
;
;       SYSTEM: FAX
;       SUBSYSTEM: Main
;
;       (C) COPYRIGHT HEWLETT-PACKARD COMPANY 1989
;                   All rights reserved
;
;       ************* HP CONFIDENTIAL *************
;
;       $Date:     07 Aug 1991 21:38:22  $
;
;       $Revision:   1.0  $
;
;       NOTES:    Asm Source file
;                 Created by Lawrence Hileman
;-----------------------------------------------------------------
;       ORIGIN:   Cardiology Business Unit
;
;       REVISIONS:
;       $Log:    I:/quarry/fax/vcs/qsafxs40.asv  $
;
;         Rev 1.0    07 Aug 1991 21:38:22   Larry_H
;       Initial revision.
;
;****************************************************************/ assume  cs:codeseg
        assume  ds:dataseg
dataseg         segment dword rw use32 public 'data'
extrn           _check_point:DWORD
dataseg         ends codeseg         segment dword er use32 public 'code'
                public  _AddCodeToOutput
                align   4

;void AddCodeToOutput( OutMsg, OutIndex, Code )
;unsigned char *OutMsg,*Code;
;unsigned int *OutIndex;
;{
;       unsigned int byte,bit,i;
;       unsigned int intcode,cd;
;
;       check_point= FAX_ADD_CODE_TO_OUTPUT;
;
;       intcode=Code[1];intcode=intcode<<24;
;       if (Code[0] > 8)        {cd=Code[2];intcode+=(cd<<16);}
;
;       for (i=0;i<Code[0];i++)
;               {
;               byte=(*OutIndex)>>3;
;               bit=(*OutIndex)&0x07;
;               if ((intcode&(0x80000000>>i)) != 0)
;                       {
;                       OutMsg[byte]= OutMsg[byte]|(0x80>>bit);
```

```
;                      )
;              *OutIndex= (*OutIndex)+1;
;              }
;}

_AddCodeToOutput          proc    near push    ebp
                mov     ebp,esp
                push    esi
                push    edi
                push    ebx
                push    edx
                push    ecx mov     word ptr ds:_check_point, 1F34h mov     esi,[ebp+12]    ; address of index
                mov     edi,[esi]       ; index
                mov     edx,[ebp+8]     ; address of output string xor     eax,eax
                mov     ebx,[ebp+16]
                mov     ax,[ebx+1]
                xchg    ah,al
                shl     eax,16
                movsx   ecx,byte ptr [ebx]

TestBit:        or      eax,eax
                jns     Next push    ecx
                mov     ebx,edi
                shr     ebx,3
                mov     ecx,edi
                and     ecx,7
                mov     al,80h
                shr     al,cl or      byte ptr [edx+ebx],al pop     ecx Next:           shl     eax,1
                inc     edi
                dec     ecx
                jnz     TestBit mov     [esi],edi mov     word ptr ds:_check_point, 1F34h pop     ecx
                pop     edx
                pop     ebx
                pop     edi
                pop     esi
                pop     ebp ret
```

```
_AddCodeToOutput    endp
codeseg     ends
            end
```

```
;*************************************************************
;
;       $Logfile:   I:/quarry/fax/vcs/qsafxs50.asv  $
;
;       FILE NAME: QSAFXS50.ASM         MODULE: Next Match
;
;       SYSTEM: FAX
;       SUBSYSTEM: Main
;
;       (C) COPYRIGHT HEWLETT-PACKARD COMPANY 1989
;                       All rights reserved
;
;       ************* HP CONFIDENTIAL **************
;
;       $Date:   07 Aug 1991 21:38:34  $
;
;       $Revision:   1.0  $
;
;       NOTES:   Asm Source file
;                Created by Lawrence Hileman
;---------------------------------------------------------------
;       ORIGIN:   Cardiology Business Unit
;
;       REVISIONS:
;       $Log:   I:/quarry/fax/vcs/qsafxs50.asv  $
;
;         Rev 1.0   07 Aug 1991 21:38:34    Larry_H
;   Initial revision.
;
;*************************************************************/
        assume   cs:codeseg
        assume   ds:dataseg
dataseg          segment dword rw use32 public 'data'
extrn            _check_point:DWORD
dataseg          ends codeseg          segment dword er use32 public 'code'
                 public  _NextMatch
                 align   4

;int NextMatch( Array, Index, Value )            /* index is a bit index */
;char *Array;
;int Index,Value;
;{
;       unsigned int byte,bit,testbit;
;
;       check_point= FAX_NEXT_MATCH;
;
;       for (;Index<LINE_LENGTH;Index++)
;               {
;               byte=(unsigned int)(Index)>>3;
;               bit=Index&0x07;
;               testbit=Array[byte]&(0x80>>bit);
;               if (Value == 0)
;                       {
;                       if (testbit != 0)
;                               return(Index);
;                       }
;               else
```

```
;                               {
;                               if (testbit == 0)
;                                       return(Index);
;                               }
;                       }
;               return(Index);
;}

_NextMatch              proc            near push            ebp
                        mov             ebp,esp
                        push            esi
                        push            ebx
                        push            edx
                        push            ecx mov             word ptr ds:_check_point, 1F35h mov             esi,[ebp+8]
                        mov             ebx,[ebp+12]
                        mov             eax,ebx
                        shr             ebx,3
                        and             eax,07h
                        mov             ecx,7
                        sub             ecx,eax
                        mov             al,[esi+ebx]
                        cmp             dword ptr [ebp+16],0
                        jz              LookForZeros
                        jmp             LookForOnes OnesLoop:               dec             ecx
                        jns             LookForOnes inc             ebx
                        mov             ecx,7
                        cmp             ebx,216
                        jz              Exit
                        mov             al,[esi+ebx]

LookForOnes:            bt              eax,ecx
                        jc              OnesLoop
                        jmp             Exit ZerosLoop:              dec             ecx
                        jns             LookForZeros inc             ebx
                        mov             ecx,7
                        cmp             ebx,216
                        jz              Exit
                        mov             al,[esi+ebx]

LookForZeros:           bt              eax,ecx
                        jnc             ZerosLoop Exit:                   shl             ebx,3
                        mov             eax,7
                        sub             eax,ecx
```

```
            add     eax,ebx
            mov     word ptr ds:_check_point, 1F35h
            pop     ecx
            pop     edx
            pop     ebx
            pop     esi
            pop     ebp
            ret _NextMatch  endp
codeseg     ends
            end
```

```
/* ::PL -m -i
/*********************************************************

$Logfile:   I:/quarry/fax/vcs/qscfxa00.c_v  $

FILE NAME: QSCFXA00.C         MODULE: change sizes

SYSTEM: FAX
    SUBSYSTEM: Algorythm (C) COPYRIGHT HEWLETT-PACKARD COMPANY 1989
              All rights reserved

************** HP CONFIDENTIAL **************

$Date:   26 Jun 1992 14:39:42  $ $Revision:   1.3  $

NOTES:   C Source file
             Created by Lawrence Hileman
------------------------------------------------------------
    ORIGIN:  Cardiology Business Unit REVISIONS:
    $Log:   I:/quarry/fax/vcs/qscfxa00.c_v  $
**
**    Rev 1.3   26 Jun 1992 14:39:42   Larry_H
** fix for long expantion strings > 5500
**
**    Rev 1.2   14 Feb 1992 15:10:36   Larry_H
** removed unnecessary log_errors
**
**    Rev 1.1   14 Feb 1992 08:08:22   Larry_H
** change how rythem leads are placed in wfcom
**
**    Rev 1.0   07 Aug 1991 21:29:42   Larry_H
** Initial revision.

***********************************************************/ include      "stdlib.h"     /* atoi prototype */ include      "qeclh005.h"   /* Config defines                   */
include      "qecfx010.h"   /* FAX resolutions and report types */ include      "qeci0007.h"   /* ID Header stuff                  */
include      "qtclh015.h"   /* ID Header structure              */
include      "qvclh015.h"   /* ID Header variable               */ include      "qeclh009.h"   /* uncompressed_ecg defines         */
include      "qtclh009.h"   /* uncompressed_ecg struct          */
include      "qvclh009.h"   /* uncompressed_ecg variable        */ include      "qeclh014.h"   /* 11 second structure defines
include      "qtclh013.h"   /* 11 second uncompressed ECG data struct
include      "qvclh013.h"   /* 11 second uncompressed ECG variabel include      "QTCFXV00.H"   /* slice defined */
```

```
#include         "qpcfxint.h"    /* Fax prototypes                */
/* check point access */
#include         "QECLSJWL.H"    /* #define check point values */
include         "qvcls02d.h"    /* extern unsigned short check_point */ define EXTRA_SAMPLES   5
define CUTOFF          1270 void ChangeSize( NewSize,config,RythStrip )
int NewSize,config;
char *RythStrip;
{
        int i,j,k,rs,si,so;

check_point= FAX_CHANGE_SIZE;

for (i=0;i<12;i++)
                {
                si=uncompressed_ecg.lead[i].sample_count;
                for (j=0,k=uncompressed_ecg.lead[i].data[si-1];j<EXTRA_SAMPLES;j
                        uncompressed_ecg.lead[i].data[si+j]=k;
                so=(si*NewSize)/250;
                ChangeSampleRate(uncompressed_ecg.lead[i].data,
                        wfcom_.ecg.lead[i],si,so);
                }

/* acals */ si=uncompressed_ecg.acal[0].sample_count;
        for (j=0,k=uncompressed_ecg.acal[0].data[si-1];j<EXTRA_SAMPLES;j++)
                uncompressed_ecg.acal[0].data[si+j]=k;
        so=(si*NewSize)/250;
        ChangeSampleRate(uncompressed_ecg.acal[0].data,
                        &wfcom_.ecg.lead[15][0],si,so);

if ((config == CONFIG_AUTO_3X4) || (config == CONFIG_AUTO_6X2))
                return;

/* rcals */
        si=uncompressed_ecg.rcal[0].sample_count;
        for (j=0,k=uncompressed_ecg.rcal[0].data[si-1];j<EXTRA_SAMPLES;j++)
                uncompressed_ecg.rcal[0].data[si+j]=k;
        so=(si*NewSize)/250;
        ChangeSampleRate(uncompressed_ecg.rcal[0].data,
                        &wfcom_.ecg.lead[16][0],si,so);

/* rythem leads */
        if (config == CONFIG_AUTO_3X4_3R)
                {
                ChangeRythemLeadsFirst( NewSize );
                return;
                }

/* must be 3x4 1R */ rs=atoi(RythStrip);

for (i=0,k=-1;(i<3)&&(k==-1);i++)
                {
```

```
                        j=uncompressed_ecg.rhy_lead[i].lead_id;
                        switch (j)
                            {
                            case CONFIG_LEAD_CODE_I:     if (rs==ECG_I)    k=i;break;
                            case CONFIG_LEAD_CODE_II:    if (rs==ECG_II)   k=i;break;
                            case CONFIG_LEAD_CODE_IIIP:
                            case CONFIG_LEAD_CODE_IIIPP:
                            case CONFIG_LEAD_CODE_III:   if (rs==ECG_III)  k=i;break;
                            case CONFIG_LEAD_CODE_AVR:   if (rs==ECG_AVR)  k=i;break;
                            case CONFIG_LEAD_CODE_AVL:   if (rs==ECG_AVL)  k=i;break;
                            case CONFIG_LEAD_CODE_AVFP:
                            case CONFIG_LEAD_CODE_AVF:   if (rs==ECG_AVF)  k=i;break;
                            case CONFIG_LEAD_CODE_C1:
                            case CONFIG_LEAD_CODE_V1:    if (rs==ECG_V1)   k=i;break;
                            case CONFIG_LEAD_CODE_C2:
                            case CONFIG_LEAD_CODE_V2P:
                            case CONFIG_LEAD_CODE_V2:    if (rs==ECG_V2)   k=i;break;
                            case CONFIG_LEAD_CODE_C3:
                            case CONFIG_LEAD_CODE_V3:    if (rs==ECG_V3)   k=i;break;
                            case CONFIG_LEAD_CODE_C4:
                            case CONFIG_LEAD_CODE_V4P:
                            case CONFIG_LEAD_CODE_V4:    if (rs==ECG_V4)   k=i;break;
                            case CONFIG_LEAD_CODE_C5:
                            case CONFIG_LEAD_CODE_V5P:
                            case CONFIG_LEAD_CODE_V5:    if (rs==ECG_V5)   k=i;break;
                            case CONFIG_LEAD_CODE_C6:
                            case CONFIG_LEAD_CODE_V6:    if (rs==ECG_V6)   k=i;break;
                            case CONFIG_LEAD_CODE_X:     if (rs==ECG_X)    k=i;break;
                            case CONFIG_LEAD_CODE_Y:     if (rs==ECG_Y)    k=i;break;
                            case CONFIG_LEAD_CODE_Z:     if (rs==ECG_Z)    k=i;break;
                            case CONFIG_LEAD_CODE_V3R:   if (rs==ECG_V3R)  k=i;break;
                            case CONFIG_LEAD_CODE_V4R:   if (rs==ECG_V4R)  k=i;break;
                            case CONFIG_LEAD_CODE_MAVRP:
                            case CONFIG_LEAD_CODE_MAVR:  if (rs==ECG_MAVR) k=i;break;
                            case CONFIG_LEAD_CODE_V7:    if (rs==ECG_V7)   k=i;break;
                            case CONFIG_LEAD_CODE_VX1:   if (rs==ECG_VX1)  k=i;break;
                            case CONFIG_LEAD_CODE_VX2:   if (rs==ECG_VX2)  k=i;break;
                            case CONFIG_LEAD_CODE_VX3:   if (rs==ECG_VX3)  k=i;break;
                            case CONFIG_LEAD_CODE_VX4:   if (rs==ECG_VX4)  k=i;break;
                            }
                        }
        if (k == -1)    k=0;
        si=uncompressed_ecg.rhy_lead[k].sample_count;
        so=(si*NewSize)/250;
        for (j=0,i=uncompressed_ecg.rhy_lead[k].data[si-1];j<EXTRA_SAMPLES;j++)
                uncompressed_ecg.rhy_lead[k].data[si+j]=i;
        if (so > 5500)
                {
                si=CUTOFF;
                so=(si*NewSize)/250;

ChangeSampleRate(uncompressed_ecg.rhy_lead[k].data,
                                wfcom_.ecg.lead[12],si,so);

si=uncompressed_ecg.rhy_lead[k].sample_count-CUTOFF;
                so=(si*NewSize)/250;

ChangeSampleRate(&uncompressed_ecg.rhy_lead[k].data[CUTOFF],
                                wfcom_.ecg.lead[13],si,so);
                }
```

```
              else
                     {
                     ChangeSampleRate(uncompressed_ecg.rhy_lead[k].data,
                                    wfcom_.ecg.lead[12],si,so);
                     }
} void ChangeRythemLeadsFirst( NewSize )
int NewSize;
{
       int i,j,k,l,si,so;

for (i=0;i<3;i++)
              {
              j=uncompressed_ecg.rhy_lead[i].lead_id;
              for (k=0;k<3;k++)
                     {
                     l=atoi(id_header.lead_map[15+k].lead_num);
                     if (l == j)      break;
                     }
              l= atoi(id_header.lead_map[15+k].chan);

si=uncompressed_ecg.rhy_lead[i].sample_count;
              so=(si*NewSize)/250;
              for (j=0,k=uncompressed_ecg.rhy_lead[i].data[si-1];j<EXTRA_SAMPL
                     uncompressed_ecg.rhy_lead[i].data[si+j]=k;

if (so > 5500)
                     {
                     si=CUTOFF;
                     so=(si*NewSize)/250;
                     }
              ChangeSampleRate(uncompressed_ecg.rhy_lead[i].data,
                            wfcom_.ecg.lead[12+l],si,so);
              }
} void ChangeRythemLeadsSecond( NewSize )
int NewSize;
{
       int i,j,k,l,si,so;

for (i=0;i<3;i++)
              {
              j=uncompressed_ecg.rhy_lead[i].lead_id;
              for (k=0;k<3;k++)
                     {
                     l=atoi(id_header.lead_map[15+k].lead_num);
                     if (l == j)      break;
                     }
              l= atoi(id_header.lead_map[15+k].chan);

si=uncompressed_ecg.rhy_lead[i].sample_count - CUTOFF;
              so=(si*NewSize)/250;

ChangeSampleRate(&uncompressed_ecg.rhy_lead[i].data[CUTOFF],
                            wfcom_.ecg.lead[12+l],si,so);
              }
}
```

```
/* ::PL -ey -ry */
/***************************************************************

$Logfile:   I:/quarry/fax/vcs/qscfxa10.c_v  $

FILE NAME: QSCFXA10.C       MODULE: Pair/Peak Pick Algorithm

SYSTEM: FAX
        SUBSYSTEM: Algorythm (C) COPYRIGHT HEWLETT-PACKARD COMPANY 1989
                    All rights reserved

************** HP CONFIDENTIAL **************

$Date:   26 Jun 1992 14:41:46  $ $Revision:   1.3  $

NOTES:    C Source file
                  Created by Lawrence Hileman
       -----------------------------------------------------------
        ORIGIN:  Cardiology Business Unit REVISIONS:
        $Log:   I:/quarry/fax/vcs/qscfxa10.c_v  $
**
**      Rev 1.3   26 Jun 1992 14:41:46   Larry_H
** fix minor errors in final string
**
**      Rev 1.2   04 Feb 1992 19:53:50   Larry_H
** don't fill in with zero, just set last sample correctly
**
**      Rev 1.1   19 Nov 1991 10:47:04   Larry_H
** set the last few samples to zero before beginning.  On long runs, they may
** get off by one.
**
**      Rev 1.0   07 Aug 1991 21:30:14   Larry_H
** Initial revision.

***************************************************************/ include        "QECLS01U.h"     /* TRUE */
include        "QECLS01V.h"     /* FALSE */ include        "qpcfxint.h"     /* Fax prototypes                  */

/* check point access */
#include        "QECLSJWL.H"     /* #define check point values */
include        "qvcls02d.h"     /* extern unsigned short check_point */

/* refer to Rick Aparo's 2/July/90 paper for algorythm steps */
/* this algorythm works well for 250s/s->300s/s and 250s/s->200s/s */
/* all other changes in sample rate must be checked */

/* the new sample length is saved as the first short int in the out sample buffe void ChangeSampleRate( InBuffer,OutBuffer,InSamples,OutSamples )
short int *InBuffer,*OutBuffer;
int InSamples,OutSamples;
```

```
{       int Nn,Nd,in,io,CorCount,straddle,i;
        short int SavedSample,NewSample,PivotSample,InterSample;
        short int min,max,min1,max1;
        int ji,jf,ni,nf;

check_point= FAX_CHANGE_SAMPLE_RATE;

FindNumDen( InSamples,OutSamples,&Nn,&Nd );
        ni=Nn/Nd;nf=Nn%Nd;
        OutBuffer[0]=(short) OutSamples;

for (i=0;i<3;i++)
                OutBuffer[OutSamples]=InBuffer[InSamples-1];

ji=jf=0;CorCount=Nd;                    /* step 1 */

SavedSample=InBuffer[0];                /* step 2 */
        PivotSample=InBuffer[0];
        NewSample=InBuffer[1];

OutBuffer[1]=SavedSample;               /* step 3 */ for (in=0,io=2;io<OutSamples;io++) /* all but last sample */
                {
                ji=0;                           /* step 4 */
                AddFloattoJ( &ji,&jf,ni,nf,Nd );
                CorCount--;
                if (CorCount == 0)
                        {
                        CorCount=Nd;
                        AddFloattoJ( &ji,&jf,0,Nd/2,Nd );
                        jf=0;
                        }
                min=PivotSample;min1=0;         /* step 5 */
                max=PivotSample;max1=0;
                FindMaxMin( &min,&min1,&max,&max1,&InBuffer[in+1],ji);
                in=in+ji;
                SavedSample=InBuffer[in];
                NewSample=InBuffer[in+1];

straddle=FALSE;                 /* step 6 */
                if ((max > OutBuffer[io-1])&&(min < OutBuffer[io-1]))
                        straddle=TRUE;

/* step 7 */
                if (straddle == FALSE)
                    {
                    if (jf == 0)
                        {                       /* step 8 */
                        if (max > OutBuffer[io-1])
                                OutBuffer[io]=max;
                            else
                                OutBuffer[io]=min;
                        PivotSample=SavedSample;
                        continue;
                        }
                    else
                        {                       /* step 9 */
                        InterSample= SavedSample +
```

```
                        ((jf*(NewSample-SavedSample))/Nd);
            if ((!(InterSample>max))&&(!(InterSample<min)))
                   {
                   if (max > OutBuffer[io-1])
                           OutBuffer[io]=max;
                       else
                           OutBuffer[io]=min;
                   PivotSample=InterSample;
                   continue;
                   }
            if (InterSample > max)   max=InterSample;
            if (InterSample < min)   min=InterSample;
                                     /* step 10 */
            if (min >= OutBuffer[io-1])
                   {
                   OutBuffer[io]=max;
                   PivotSample=InterSample;
                   continue;
                   }
            if (max <= OutBuffer[io-1])
                   {
                   OutBuffer[io]=min;
                   PivotSample=InterSample;
                   continue;
                   }
            straddle=TRUE;
            }
     }
                                      /* step 11, straddle=TRUE; */
ji=0;
AddFloattoJ( &ji,&jf,ni,nf,Nd );
CorCount--;
if (CorCount == 0)
       {
       CorCount=Nd;
       AddFloattoJ( &ji,&jf,0,Nd/2,Nd );
       jf=0;
       }
min1=min1-ni-1;
max1=max1-ni-1;
FindMaxMin( &min,&min1,&max,&max1,&InBuffer[in+1],ji);
in=in+ji;
SavedSample=InBuffer[in];
NewSample=InBuffer[in+1];

if (jf == 0)
       {
       if (max1 > min1)
              {
              OutBuffer[io++]=min;
              OutBuffer[io]=max;
              }
          else
              {
              OutBuffer[io++]=max;
              OutBuffer[io]=min;
              }
       PivotSample=SavedSample;
       continue;
       }
```

```
            InterSample= SavedSample+((jf*(NewSample-SavedSample))/Nd);
            i=0;
            if (nf > Nd/2)   i=1;
            if (InterSample > max)   {max=InterSample;maxl=2*ni+i+2;}
            if (InterSample < min)   {min=InterSample;minl=2*ni+i+2;} if (maxl > minl)
                    {
                    OutBuffer[io++]=min;
                    OutBuffer[io]=max;
                    }
                else
                    {
                    OutBuffer[io++]=max;
                    OutBuffer[io]=min;
                    }
            PivotSample=InterSample;
            }
}
void AddFloattoJ( ji,jf,ni,nf,Nd )
int *ji,*jf,ni,nf,Nd;
{
        *jf=*jf+nf;
        *ji=*ji+ni;
        while (*jf >= Nd)
                {
                *ji=*ji+1;*jf=*jf-Nd;
                }
}
```

```
/* ::PL -ey -ry */
/***************************************************************

$Logfile:   I:/quarry/fax/vcs/qscfxa20.c_v  $

FILE NAME: QSCFX102.C          MODULE: Find Max and Min

SYSTEM: FAX
     SUBSYSTEM: Algorythm (C) COPYRIGHT HEWLETT-PACKARD COMPANY 1989
                All rights reserved

************** HP CONFIDENTIAL **************

$Date:    07 Aug 1991 21:30:38  $ $Revision:   1.0  $

NOTES:   C Source file
              Created by Lawrence Hileman
-----------------------------------------------------------------
     ORIGIN:  Cardiology Business Unit REVISIONS:
     $Log:   I:/quarry/fax/vcs/qscfxa20.c_v  $
**
**    Rev 1.0   07 Aug 1991 21:30:38    Larry_H
** Initial revision.

****************************************************************/ include        "qpcfxint.h"    /* Fax prototypes               */

/* check point access */
#include        "QECLSJWL.H"    /* #define check point values */
include        "qvcls02d.h"    /* extern unsigned short check_point */

/* refer to Rick Aparo's 2/July/90 paper for algorythm steps */ void FindMaxMin( min,minl,max,maxl,InBuffer,j)
short int *min,*max,*minl,*maxl;
short int *InBuffer;
int j;
{
        int i;

check_point= FAX_FIND_MAX_MIN;
        for (i=0;i<j;i++)
             {
                if (InBuffer[i] > *max)
                     {
                     *max=InBuffer[i];
                     *maxl=(short)(i+1);
                     }
                if (InBuffer[i] < *min)
                     {
                     *min=InBuffer[i];
                     *minl=(short)(i+1);
                     }

}
}
```

```
/* ::PL -ey -ry */
/*************************************************************

$Logfile:   I:/quarry/fax/vcs/qscfxa30.c_v  $

FILE NAME: QSCFXA30.C         MODULE: Find Numerator/demoniator

SYSTEM: FAX
    SUBSYSTEM: Algorythm (C) COPYRIGHT HEWLETT-PACKARD COMPANY 1989
               All rights reserved

************** HP CONFIDENTIAL **************

$Date:    07 Aug 1991 21:31:02  $ $Revision:   1.0  $

NOTES:   C Source file
             Created by Lawrence Hileman
------------------------------------------------------------
    ORIGIN:  Cardiology Business Unit REVISIONS:
    $Log:    I:/quarry/fax/vcs/qscfxa30.c_v  $
**
**    Rev 1.0   07 Aug 1991 21:31:02   Larry_H
** Initial revision.

*************************************************************/ include       "qpcfxint.h"   /* Fax prototypes              */

/* check point access */
#include       "QECLSJWL.H"   /* #define check point values */
#include       "qvcls02d.h"   /* extern unsigned short check_point */

/* this function will provide the closest reduced rational number as */
/* Num and Den. for 250->200 Num=5,Den=4. for 250->300 Num=5,Den=6 */ static int GCD( u,v )
int u,v;
{
        if (v == 0)    return( u );
        return( GCD( v, u%v ) );
} void FindNumDen( InputSamples,OutputSamples,Num,Den )
int InputSamples,OutputSamples;
int *Num,*Den;
{
        int i;

check_point= FAX_FIND_NUM_DEN;
        i= GCD( InputSamples, OutputSamples );

*Num= InputSamples/i;
        *Den= OutputSamples/i;
}
```

We claim:

1. A method of interactive imaging comprising the steps of: providing a digital database at a physical location defining a database site;

forming an image comprising a representation of data stored in the database, the stored data including (1) a physiological waveform portion recorded for a particular patient, (2) identification data for uniquely identifying the database, and (3) a commentary portion for receiving diagnostic commentary pertaining to the physiological waveform data stored in the database;

automatically sizing and locating said commentary portion relative to said physiological waveform portion in a manner which prevents overlap of said commentary portion and said physiological waveform portion;

transmitting the image to the remote site;

at the remote site, annotating the image with diagnostic commentary pertaining to the data stored in the database;

transmitting that annotated facsimile image back to the database site; and at the database site, recovering the identification data from the annotated facsimile image to identify the database and updating the identified database so as to include the diagnostic commentary pertaining to the data stored in the database without altering the previously stored data.

2. A method according to claim 1 wherein said transmitting the facsimile image includes:

establishing a fax connection between the database site and the remote site;

selecting a fax resolution based upon a fax protocol dialogue between the database site and the remote site;

converting the image to a fax format having the selected fax resolution; and faxing the image to the remote site.

3. A method according to claim 2 wherein:

the stored data includes waveform data representable as a waveform; and said forming an image includes resizing the waveform so as to fully utilize the selected fax resolution.

4. A method according to claim 2 wherein:

the stored data includes alphanumeric data; and said forming an image includes converting the alphanumeric data to a bit map image form at the selected fax resolution, thereby forming a text report portion of the image for displaying the alphanumeric data in a graphic form at the remote site.

5. A method according to claim 4 wherein the alphanumeric data includes the identification data and the text report includes a blank dedicated field for receiving an annotation added to the image at the remote site.

6. A method according to claim 1 wherein updating the database includes:

determining a location of the diagnostic commentary pertaining to the data stored in the database in the annotated image;

extracting an image of the diagnostic commentary pertaining to the data stored in the database from the said location; and storing the extracted image of the diagnostic commentary pertaining to the data stored in the database in the identified database.

7. A method according to claim 1 further comprising:

converting the stored identifying data into a machine-readable graphic form; and wherein:

said forming the image includes adding the graphic form identifying data into the image.

8. A method acording to claim 7 wherein said converting step includes converting the identifying data into a bar-code format to facilitate reading the identifying data from the annotated image.

9. A method according to claim 1 wherein:

forming an image at the database site includes providing a blank dedicated field having a predetermined size and location within the image as the commentary portion for receiving diagnostic commentary pertaining to the data stored in the database;

said annotating step includes inserting a comment with the blank dedicated field at the remote site; and updating the database includes extracting an image from a location in the annotated image corresponding to the said predetermined location, and storing the extracted image in the database, whereby the updated database includes both the data originally stored in the database and an image of the annotation.

10. A method of interactive imaging comprising the steps of:

forming an image comprising a representation of data stored in the database, the stored image including identification data for uniquely identifying the database, and a commentary portion for receiving diagnostic commentary pertaining to the data stored in the database;

establishing a fax connection between the database site and the remote site;

selecting a fax resolution based upon a fax protocol dialogue between the database site and the remote site;

partitioning the image to form a predetermined number of columns and, for each such column:

rasterizing a corresponding text report portion to form bit map data;

adding a corresponding waveform data portion to the bit map data;

fax encoding the column of bit map data for fax transmission, thereby faxing an image that includes both the text report portion and the waveform portion;

faxing the image to the remote site; and at the remote site, annotating the image with diagnostic commentary pertaining to the data stored in the database and transmitting that annotated image back to the database site; and at the database site, recovering the identification data from the annotated image to identify the database and updating the identified database so as to include the diagnostic commentary pertaining to the data stored in the database without altering the previously stored data.

11. A method according to claim 10 further comprising, for each column, adding data defining a corresponding portion of an overlay grid to the bit map data, so that the image includes a grid superimposed over the waveform.

12. A method of interactive imaging comprising the steps of:

providing a digital database at a physical location defining a database site;

forming an image at the database site, comprising a representation of data stored in the database, the stored data including identification data for uniquely identifying the database and a blank field commentary portion for receiving diagnostic commentary pertaining to the data stored in the database having a predetermined size and location within the image;

wherein the image includes a waveform portion;

selecting the dedicated field size and location so that the dedicated field commentary portion of the image does not overlap the waveform portion in the image transmitting the image to a site remote from the database;

at the remote site annotating the image with diagnostic commentary pertaining to the data stored in the database within the blank field commentary portion and transmitting that annotated image back to the database site; and at the database site, recovering the identification data from the annotated image to identify the database and updating the identified data from the annotated image to identify the database updating the identified database so as to include the diagnostic commentary pertaining to the data stored in the database without altering the previously stored data whereby the updated database includes both the data originally stored in the database and an image of the annotation.

13. A method of interactive electrocardiograph imaging between an instrument site and a remote site, comprising the steps of:

recording an ECG of a patient at the instrument site;

storing the recorded ECG in a digital database, the database including unique identification data for identifying the database;

converting the ECG data so as to form a fax image;

adding the identification data to the fax image;

locating a diagnostic commentary portion in said fax image in a manner which avoids overlapping of said ECG;

faxing the fax image to the remote site for review;

at the remote site, annotating the fax image by inserting at least one diagnostic comment in said diagnostic commentary portion;

faxing the annotated ECG image back to the instrument site;

at the instrument site, recovering the identification data from the annotated image to identify the database; and updating the identified database by moving a portion of the annotated image containing the at least one diagnostic comment into the identified database.

14. A method according to claim 13 further comprising encoding the identification data into a machine-readable bar-code form.

15. A method according to claim 13 further comprising providing a blank dedicated area as said diagnostic commentary portion at a predetermined location within the fax format image for the at least one diagnostic comment; and wherein annotating the fax image includes inserting the at least one diagnostic comment within the dedicated area; and said moving step includes copying a portion of the annotated image corresponding to the said location into the database, thereby extracting the at least one diagnostic comment from the annotated image.

16. A method of interactive electrocardiograph imaging between an instrument site and a remote site comprising the steps of:

recording an ECG of a patient at the instrument site:

storing the recorded ECG in a digital database, the database including unique identification data for identifying the database:

converting the ECG data so as to form a fax image;

adding the identification data to the fax image:

faxing the fax image to the remote site for review;

inserting a predetermined first delimit mark on the fax image to indicate the start of a comment area for at least one diagnostic comment;

inserting a predetermined second delimit mark on the fax image to indicate an end of the comment area;

at the remote site, inserting the at least one diagnostic comment intermediate the first and second delimit marks;

faxing the annotated ECG image back to the instrument site;

at the instrument site, recovering the identification data from the annotated image to identify the database;

detecting the first and second delimit marks;

defining a comment area intermediate the detected delimit marks;

extracting an image of the at least one diagnostic comment area from the annotated image; and writing the extracted image of the at least one diagnostic comment into the identified database.

17. A method according to claim 16 wherein said defining a comment area includes defining a generally rectangular strip located intermediate the detected delimit marks.

18. A method of interactive electrocardiograph imaging between an instrument site and a remote site, comprising the method steps of:

recording an ECG of a patient at the instrument site;

storing the recorded ECG in a digital database, the database including unique identification data for identifying the database;

converting the ECG data so as to form a fax image;

adding the identification data to the fax image;

faxing the fax image to the remote site for review;

inserting a predetermined delimit mark on the fax image to indicate a location of a comment area for the at least one diagnostic comment;

at the remote site, annotating the fax image by inserting at least one diagnostic comment;

faxing the annotated ECG image back to the instrument site;

at the instrument site, recovering the identification data from the annotated image to identify the database;

detecting the delimit mark;

defining a comment area having predetermined dimensions and extending from the indicated location;

extracting an image of the defined comment area from the annotated image; and writing the extracted image of the comment into the identified database in order to update the database.

19. A system for remote interactive medical imaging via fax telecommunications, comprising:

an instrument for acquiring physiological input data from a patient defining a waveform;

digital data storage means coupled to the instrument for storing digital image data representing the waveform in a database;

means for storing alphanumeric data associated with the patient in the database;

means for converting the waveform image data and the alphanumeric data into a single bit map image and for including in the single bit map a diagnostic commentary field and for locating said diagnostic commentary field in a particular position relative to said waveform image data in order to avoid overlapping of said waveform image data;

means for converting the bit map image to form a first fax file without optical scanning; and fax means coupled to the converting means for faxing the first fax file to a remote site for review.

20. A system according to claim 19 further comprising:

means at the remote site for receiving the first fax file;

means coupled to the receiving means for displaying the bit map image for examination by a user at the remote site;

means for annotating the displayed bit map image in the region of the diagnostic commentary field to form an annotated image;

means for converting the annotated image so as to form a second fax file for transmission back to the instrument site;

means at the instrument site for identifying the database from the annotated image; and means for extracting the annotation from the diagnostic commentary field of the annotated image.

* * * * *